United States Patent
Nanjo et al.

(10) Patent No.: US 12,060,374 B2
(45) Date of Patent: Aug. 13, 2024

(54) SILYL ETHER-CONTAINING SULFONATE SALT

(71) Applicants: National University Corporation Tottori University, Tottori (JP); Nisshinbo Holdings Inc., Tokyo (JP)

(72) Inventors: Masato Nanjo, Tottori (JP); Gen Masuda, Chiba (JP)

(73) Assignees: NATIONAL UNIVERSITY CORPORATION TOTTORI UNIVERSITY, Tottori (JP); NISSHINBO HOLDINGS INC., Tokyo (JP)

( * ) Notice: Subject to any disclaimer, the term of this patent is extended or adjusted under 35 U.S.C. 154(b) by 472 days.

(21) Appl. No.: 17/433,287

(22) PCT Filed: Feb. 4, 2020

(86) PCT No.: PCT/JP2020/004134
§ 371 (c)(1),
(2) Date: Aug. 24, 2021

(87) PCT Pub. No.: WO2020/175035
PCT Pub. Date: Sep. 3, 2020

(65) Prior Publication Data
US 2022/0135602 A1    May 5, 2022

(30) Foreign Application Priority Data
Feb. 27, 2019 (JP) .................. 2019-033856

(51) Int. Cl.
| | |
|---|---|
| *C07F 7/08* | (2006.01) |
| *H01G 11/60* | (2013.01) |
| *H01M 10/0567* | (2010.01) |
| *H01M 10/0569* | (2010.01) |

(52) U.S. Cl.
CPC ....... *C07F 7/0838* (2013.01); *H01M 10/0567* (2013.01); *H01M 10/0569* (2013.01); *H01G 11/60* (2013.01); *H01M 2300/0045* (2013.01)

(58) Field of Classification Search
CPC .............................. C07F 7/0838; C07F 9/5407
See application file for complete search history.

(56) References Cited

U.S. PATENT DOCUMENTS 4,814,471 A    3/1989   Renauld

FOREIGN PATENT DOCUMENTS

| FR | 2.147.768 A1 | 3/1973 |
| FR | 2147768 A1 * | 3/1973 |
| JP | 63-243088 A | 10/1988 |

OTHER PUBLICATIONS

M. J. Owen, 3 Chem., Phys. Chem. Anwendungstech. Grenzflaechenaktiven Stoffe, Ber. Int. Kongr. 623-630 (1973) (Year: 1973).*
Registry online, Oct. 5, 2004, retrieved on Apr. 8, 2020, retrieved from: STN, CAS registration No. 757130-01-1, entire text, cited in ISR (1 page).
Registry online, Nov. 16, 1984, retrieved on Apr. 8, 2020, retrieved from: STN, CAS registration No. 50663-06-4, entire text. cited in ISR (1 page).
Huang et al., "Synthesis , Properties, and Aggregation Behavior of Tetrasiloxane-Based Anionic Surfactants", Langmuir, 2018, vol. 34, No. 14, pp. 4382-4389, Fig. 1, cited in ISR (8 page).
Registry online, Aug. 9, 2018, retrieved on Apr. 8, 2020, retrieved from: STN, CAS registration No. 2237219-69-9, entire text, cited in ISR (1 page).
International Search Report dated Apr. 28, 2020, issued in counterpart International Application No. PCT/JP2020/004134 (3 pages).

* cited by examiner

*Primary Examiner* — Alexander R Pagano
*Assistant Examiner* — Frank S. Hou
(74) *Attorney, Agent, or Firm* — WHDA, LLP

(57) ABSTRACT

Provided is a silyl ether-containing sulfonate salt that contains an anion represented by formula (1) and a cation.

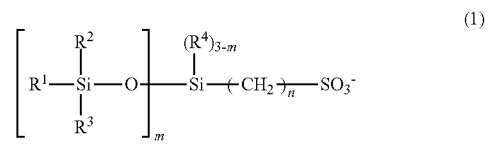

(In the formula, $R^1$ to $R^4$ are each independently a C1-4 alkyl group. m is an integer from 1 to 3. n is an integer from 2 to 8.)

10 Claims, 22 Drawing Sheets

SILYL ETHER-CONTAINING SULFONATE SALT

TECHNICAL FIELD

The present invention relates to a silyl ether-containing sulfonate salt.

BACKGROUND ART

An ionic liquid refers to a salt composed only of ions and generally having a melting point of 100° C. or lower. Various application studies have been made on the ionic liquid from its characteristics. In many ionic liquids known so far, an anion contains a halogen atom such as a fluorine atom. This causes still a problem in terms of an environmental load, whereby a halogen-free ionic liquid is desired.

SUMMARY OF INVENTION

Technical Problem

The present invention has been made in view of the above circumstances, and an object thereof is to provide a novel salt that can be an ionic liquid free of halogen atom.

Solution to Problem

As a result of intensive studies to achieve the above object, the present inventors have found that the above object can be achieved by a sulfonate salt having a silyl ether structure, and have completed the present invent on.

That is, the present invention provides the following silyl ether-containing sulfonate salt.

1. A silyl ether-containing sulfonate salt containing: an anon having the following formula (1); and a cation,

[Chem. 1]

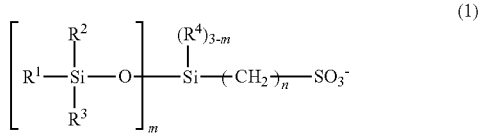

(1)

wherein: $R^1$ to $R^4$ are each independently an alkyl group having 1 to 4 carbon atoms; m is an integer of 1 to 3; and n is an integer of 2 to 8.

2. The salt according to 1, wherein $R^1$ to $R^3$ are the same group.
3. The salt according to 2, wherein $R^1$ to $R^3$ are a methyl group.
4. The salt according to 1, wherein $R^1$ is a group different from $R^2$ and $R^3$, and $R^2$ and $R^3$ are the same group.
5. The salt according to 4, wherein $R^1$ is an alkyl group having 2 to 4 carbon atoms, and $R^2$ and $R^3$ are a methyl group.
6. The salt according to any of 1 to 5, wherein in is 1 or 2.
7. The salt according to any of 1 to 6, wherein $R^4$ is a methyl group.
8. The salt according to any of 1 to 7, wherein n is 2 or 3.
9. The salt according to any of 1 to 8, wherein the cation is an organic cation.
10. The salt according to 9, wherein the cation is a phosphorus atom-containing organic cation.
11. The salt according to 9, wherein the ca a is a nitrogen atom-containing organic cation.
12. The salt according to any one of 1 to 11, wherein the salt is an ionic liquid having a melting point of 100° C. or lower.
13. The salt according to 12 wherein the salt is an ionic liquid having a melting point 25° or lower.

Advantageous Effects of Invention

The sill ether-containing sulfonate salt of the present invention becomes an ionic liquid depending on the type of a cation, and is halogen-free, whereby it has a low environmental load.

DESCRIPTION OF EMBODIMENTS

[Silyl Ether-Containing Sultanate Salt]

Figure 1:
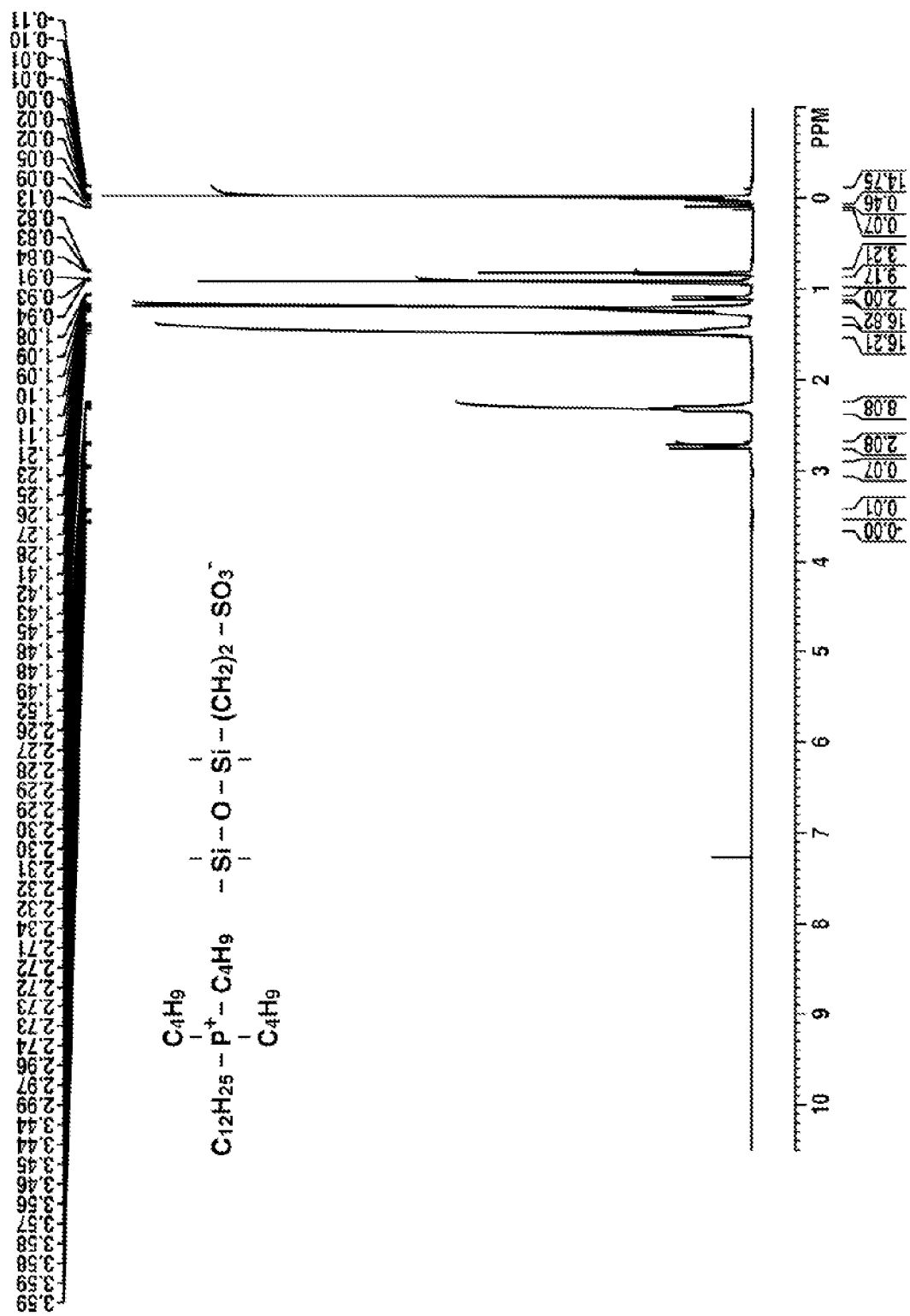
FIG. 1 is a $^1$H-NMR spectrum of BDDP MeSilC$_2$SO$_3$ prepared in Example 2-1.

A silyl ether-containing sulfonate salt of the present invention contains an anion having the following formula (I) and a cation.

[Chem. 2]

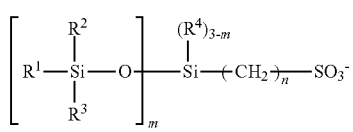

(1)

In the formula (1), $R^1$ to $R^4$ are each independently an alkyl group having 1 to 4 carbon atoms. The alkyl group may be linear, branched, or cyclic, and specific examples thereof include a methyl group, an ethyl group, an n-propyl group, an isopropyl group, a cyclopropyl group, an n-butyl group, a sec-butyl group, an isobutyl group, a tert-butyl and a cyclobutyl group. Among them, $R^1$ to $R^3$ are preferably a linear alkyl group having 1 to 4 carbon atoms.

$R^1$ to $R^3$ are preferably all the same group, more preferably all methyl groups or ethyl groups, and still more preferably all methyl groups. It is also preferable that $R^1$ is a group different from $R^2$ and $R^3$, and $R^2$ and $R^3$ are the same group. At this time, it is more preferable that $R^1$ is an alkyl group having 2 to 4 carbon atoms, and $R^2$ and $R^3$ are a methyl group.

$R^4$ is preferably a linear alkyl group having 1 to 4 carbon atoms, more preferably a methyl group or an ethyl group, and still more preferably a methyl group.

In the formula (1), m is an integer of 1 to 3, and preferably 1 or 2. n is an integer of 2 to 8, preferably 2 to 6, and more preferably 2 or 3.

The cation contained in the silyl ether-containing sulfonate salt of the present invention is not particularly limited, but is preferably a monovalent cation. The cation may be an inorganic cation or an organic cation, but is preferably an organic cation.

Examples of the inorganic cation include alkali metal ions such as a sodium ion, a potassium ion, and a lithium ion, and metal ions such as a magnesium ion, a silver ion, a zinc ion, and a copper ion.

As the organic cation, a phosphorus atom-containing organic cation and a nitrogen atom-containing organic cation are preferable, and specifically, a quaternary phosphonium ion, a quaternary ammonium ion, an imidazolium ion, a pyridinium ion, a pyrrolidinium ion, and a piperidinium ion and the like are preferable.

The phosphorus atom-containing organic cation is preferably, for example, a quaternary phosphonium ion having the following formula (2).

[Chem. 3]

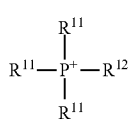

(2)

In the formula (2), $R^{11}$ is an alkyl group having 1 to 20 carbon atoms. The alkyl group having 1 to 20 carbon atoms may be linear, branched, or cyclic, and specific examples thereof include, in addition to the above-described alkyl group having 1 to 8 carbon atoms, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-eicosyl group.

In the formula (2), $R^{12}$ is an alkyl group having 1 to 20 carbon atoms or an alkoxyalkyl group of —$(CH_2)_k$—OR. k is 1 or 2. R is a methyl group or an ethyl group. Examples of the alkyl group hiving 1 to 20 carbon atoms include those described above. Examples of the alkoxyalkyl group include a methoxymethyl group, an ethoxymethyl group, a methoxyethyl group, and an ethoxyethyl group. Among the alkoxyalkyl groups, a methoxymethyl group or a methoxyethyl group is preferable.

Among the quaternary phosphonium ions having the formula (2), those in which $R^{12}$ is an alkoxyalkyl group of —$(CH_2)_k$—OR are likely to form an ionic liquid. When $R^{12}$ is an alkyl group, those having a structure in which $R^{11}$ and $R^{12}$ are different from each other are likely to form an ionic liquid. In this case, the difference in the number of carbon atoms is preferably 1 or more, more preferably 2 or more, and still more preferably 4 or more.

As the nitrogen atom-containing organic cation, for example, one having the following formula (3) is preferable.

[Chem. 4]

(3)

In the formula (3), $R^{21}$ to $R^{24}$ are each independently an alkyl group having 1 to 20 carbon atoms or an alkoxyalkyl group of —$(CH_2)_k$—OR. k is 1 or 2. R is a methyl gory or an ethyl group. Examples of the alkyl group having 1 to 20 carbon atoms and the alkoxyalkyl group include the same groups as those described above.

Any two of $R^{21}$ to $R^{24}$ may be bonded to each other to form a ring with a nitrogen atom to which they are bonded. Furthermore, any two of $R^{21}$ to $R^{24}$ may be bonded to each other to form a ring with a nitrogen atom to which they are bonded, and the remaining two may also be bonded to each other to form a spiro ring having a nitrogen atom as a spiro atom. In this case, examples of the ring include an uridine ring, an azetidine ring, a pyrrolidine ring, a piperidine ring, and an azepane ring, but a pyrrolidine ring and a piperidine ring and the like are preferable, and a pyrrolidine ring and the like is more preferable. As the spiro ring, a 1,1'-spirobipyrrolidine ring is particularly preferable.

When $R^{21}$ to $R^{24}$ are all alkyl groups, those in which at least one of $R^{21}$ to $R^{24}$ has a structure different from the others are likely to form an ionic liquid. In this case, the difference in the number of carbon atoms is preferably 1 or more, more preferably 2 or more, and still more preferably 4 or more.

Specific examples of the nitrogen atom-containing organic cation having the formula (3) include a quaternary ammonium ion having the following formula (3-1) or (3-2) and a pyrrolidinium ion having the following formula (3-3) or (3-4).

[Chem. 5]

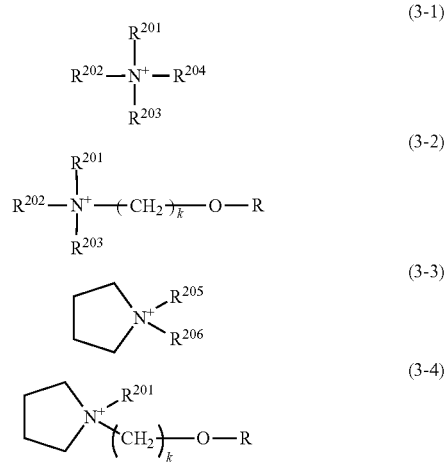

(3-1)
(3-2)
(3-3)
(3-4)

In the formulae (3-1) to (3-4), R and k are the same as described above. $R^{201}$ to $R^{204}$ are each independently an alkyl group having 1 to 4 carbon atoms. $R^{205}$ and $R^{206}$ are each independently an alkyl group having 1 to 4 carbon atoms. $R^{205}$ and $R^{206}$ may be bonded to each other to form a ring with a nitrogen atom to which they are bonded. Examples of the alkyl group having 1 to 4 carbon atoms include the same groups as those described above.

As the nitrogen atom-containing organic cation, for example, an imidazolium ion hiving the following formula (4) is also preferable.

[Chem. 6]

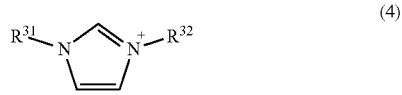

(4)

In the formula (4), $R^{31}$ and $R^{32}$ are each independently an alkyl group having 1 to 20 carbon atoms or an alkoxyalkyl group of —$(CH_2)_k$—OR. R and k are the same as described above. Examples of the alkyl group having 1 to 20 carbon atoms and the alkoxyalkyl group include the same groups as those described above. In this case, it is likely to form an ionic liquid when $R^{31}$ and $R^{32}$ are different groups from each other.

As the nitrogen atom-containing organic cation, for example, a pyridinium ion having the following formula (5) is also preferable.

[Chem. 7]

(5)

In the formula (5), $R^{41}$ is an alkyl group having 1 to 8 carbon atoms or an alkoxyalkyl group of —$(CH_2)_k$—OR. R and k are the same as described above. Examples of the alkyl group having 1 to 8 carbon atoms and the alkoxyalkyl group include the same groups as those described above.

The silyl ether-containing sulfonate salt of the present invention becomes an ionic liquid depending on the type of a cation. For example, those in which the cation has the formula (3-4) are likely to be an ionic liquid. Among those having the formula (2), those, having a structure in which $R^{11}$ and $R^{12}$ are different from each other are likely to be an ionic liquid. In the present invention, the ionic liquid means a salt composed only of ions and having a melting point of 100° C. or lower. The ionic liquid composed of the silyl ether-containing sulfonate salt of the present invention preferably has a melting point of room temperature (25° C.) or lower (that is, a liquid at room temperature). The ionic liquid composed of the silyl ether-containing sulfonate salt of the present invention is halogen-free, whereby it has a low environmental load.

[Method for Producing Silyl Ether-Containing Sulfonate Salt]

The silyl ether-containing sulfonate salt of the present invention can be produced, for example, according to the following scheme A:

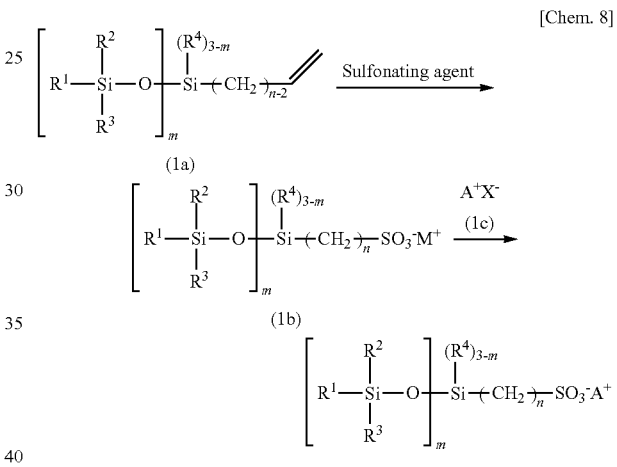

[Chem. 8]

wherein: $R^1$ to $R^4$, m, and n are the same as described above; $M^+$ is a metal ion; $A^+$ is a monovalent cation; and $X^-$ is a halide ion.

First, a compound (1a) is reacted with a sulfonating agent to synthesize a compound (1b) (first step). Examples of the sulfonating agent include sodium bisulfite. The compound (1a) can be synthesized with reference to J. Org. Chem., 1970, 35, pp. 1308-1314. The sulfonation can be performed with reference to J. Org. Chem., 1961, 26 (6), pp. 2097-2098.

Examples of the solvent used in the first step include only water, or mixed solvents obtained by adding alcohols such as methanol and ethanol, or hydrophilic solvents such as acetone and acetonitrile as auxiliary solvents to water. A reaction temperature is usually about 10 to 50° C., and preferably about 20 to 30° C. A reaction time is usually about 1 to 7 days, and preferably about 3 or 4 days.

Next, an ion exchange reaction between the compound (1b) and a compound (1c) is performed (second step). Thereby, a salt containing an anion having the formula (1) can be obtained.

The ion exchange reaction can be performed, for example, by mixing aqueous solution of the compound (1b) with an aqueous solution of the compound (1c). A reaction temperature at this time is preferably 10 to 50° C., and more preferably around room temperature (around 25° C.). A reaction time is usually about 3 or 4 days. When the compound (1b) and the compound (1c) are mixed, an organic solvent may be used as long as it dissolves both the compounds without being limited to the aqueous solution.

In the reaction of the second step, the use ratio of the compound having the formula (1b) and the compound having the formula (1c) can be set to about 5:1 to 1:5 in terms of molar ratio, but in consideration of cost, the reaction is preferably performed at a ratio close to 1:1.

After the completion of the reaction, a desired product can be obtained by performing a normal post-treatment.

The silyl ether-containing sulfonate salt of the present invention can be also used as an electrolyte solvent, an electrolyte and an additive for electrolytes for electric storage devices such as an electric double layer capacitor, a lithium ion capacitor, a redox capacitor, a lithium secondary battery, a lithium ion secondary battery, a lithium air battery, and a proton polymer battery. The silyl ether-containing sulfonate salt of the present invention can also be used as a lubricant. Furthermore, the silyl ether-containing sulfonate salt of the present invention can also be used as an antistatic agent or a plasticizer added to polymer materials such as rubber and plastics. Since the ionic liquid composed of the silyl ether-containing sulfonate salt of the present invention is a halogen-free ionic liquid, it is useful as a green solvent with a lower environmental load.

EXAMPLES

Hereinafter, the present invention is described in more detail with reference to Examples, but the present invention is not limited to the following Examples. Analysis apparatuses and conditions used in Examples are as follows.

[1] Nuclear Magnetic Resonance ($^1$H-NMR, $^{13}$C-NMR, $^{29}$Si-NMR) Spectrum
  Apparatus: ECX-500 ($^1$H-NMR, $^{13}$C-NMR, $^{29}$Si-NMR) manufactured by JEOL Ltd., or ECZ-400S ($^1$H-NMR) manufactured by JEOL Ltd.
  Solvent: deuterated dimethyl sulfoxide (DMSO-$d_6$) or deuterated chloroform (CDCl$_3$)

[2] Melting Point
  Apparatus: DSC 6200 manufactured by Seiko Instruments Inc.
  Measurement conditions:
    the temperature was raised from 20° C. to 40° C. at a rate of 10° C./min and held at 40° C. for 1 minute, then lowered from 40° C. to −100° C. at 1° C./min and held at −100° C. for 1 minute, and subsequently raised from −100° C. to 100° C. at 1° C./min.

[Example 1-1] Synthesis of Sodium 2-(1',1',3',3',3'-pentamethyldisiloxanyl)ethane-1-sulfonate (MeSilC$_2$SO$_3$Na)

A three-necked flask equipped with a reflux condenser and a magnetic stirrer was degassed, and 7.3 g (70.1 mmol) of sodium bisulfite, 0.8 g (11.5 mmol) of sodium nitrite, 0.8 g (9.4 mmol) of sodium nitrate, 60 mL of ion-exchanged water, 6.0 g (34.7 mmol) of pentamethylvinyldisiloxane, and 130 mL of methanol were charged into the flask under a nitrogen stream. The mixture was vigorously stirred at room temperature for 3 days in a sealed state. The precipitated solid was removed by suction filtration, and methanol was distilled off from the filtrate by atmospheric distillation. Then, the precipitated colorless crystal was filtered off to obtain a desired compound MeSilC$_2$SO$_3$Na (yield amount: 6.5 g (17.7 mmol), yield amount: 51.0%).

$^1$H-NMR (DMSO-$d_6$, 500 MHz, δ)
3.43 (s, 10H), 2.37 (m, 2H), 0.85 (m, 2H), 0.05 (s, 9H), 0.03 (s, 6H).
$^{13}$C-NMR (DMSO-$d_6$, 125 Hz, δ)
45.9 (—CH$_2$—SO$_3$NA), 13.8 (—CH$_2$—CH$_2$—SO$_3$Na), 2.2 (—Si(CH$_3$)$_4$), 0.3 (—Si(CH$_3$)$_2$—).
$^{29}$Si-NMR (DMSO-$d_6$, 100 MHz, δ) 8.0.

[Example 1-2] Synthesis of sodium 3-(1',1',3',3',3'-pentamethyldisiloxanyl)propane-1-sulfonate (MeSilC$_3$SO$_3$Na)

MeSilC$_3$SO$_3$Na was obtained as a colorless solid (yield amount: 2.9 g (9.8 mmol), yield amount: 36.4%) in the same manner as in Example 1-1 except that 5.1 g (27.0 mmol) of allylpentamethyldisiloxane was used in place of 6.0 g of pentamethylvinyldisiloxane.

$^1$H-NMR (DMSO-$d_6$, 500 MHz, δ)
3.28 (s, 2H), 2.32 (m, 2H), 1.47 (m, 2H), 0.38 (m, 2H), −0.08 (s, 9H), −0.11 (s, 6H).
$^{13}$C-NMR (DMSO-$d_6$, 125 Hz, δ)
55.1 (—CH$_2$—SO$_3$Na), 18.91 (—CH$_2$—CH$_2$—SO$_3$Na), 17.5 (CH$_2$—CH$_2$—CH$_2$—SO$_3$Na), 2.0 (—Si(CH$_3$)$_3$), 0.4 (—Si(CH$_3$)$_2$—).
$^{29}$Si—NMR (DMSO-$d_6$, 100 MHz, δ) 8.5.

[Example 1-3] Synthesis of Sodium 2-(3'-n-butyl-1',1',3',3'-tetramethyldisiloxanyl)ethane-1-sulfonate (BuSilC$_2$SO$_3$Na)

BuSilC$_2$SO$_3$Na was obtained as a colorless solid in the same manner as in Example 1-1 except that 5.0 g (21.8 mmol) of 3-n-butyl-1,1,3,3-tetramethyl-1-vinyldisiloxane was used in place of 6.0 g of pentamethylvinyldisiloxane (yield amount: 5.2 g (12.6 mmol), yield amount: 55.4%).

$^1$H-NMR (DMSO-$d_6$, 500 MHz, δ)
3.65 (s, 10H), 2.55 (m, 2H), 1.45 (m, 4H), 1.04 (m, 5H), 0.66 (m, 2H), 0.21 (s, 6H), 0.20 (s, 6H).
$^{13}$C-NMR (DMSO-$d_6$, 125 Hz, δ)
45.9, 25.8, 25.1, 17.6, 13.7, 0.5, 0.3.
$^{29}$Si—NMR (DMSO-$d_6$, 100 MHz, δ) 8.4, 7.8.

[Example 1-4] Synthesis of Sodium 3-(3'-n-butyl-1',1',3',3'-tetramethyldisiloxisanyl)-propane-1-sulfonate (BuSilC$_3$SO$_3$Na)

BuSilC$_3$SO$_3$Na was obtained as a colorless solid in the same manner as in Example 1-1 except that 5.0 g (21.8 mmol) of 1-allyl-3-n-butyl-1,1,3,3-tetramethyldisiloxane was used in place of 6.0 g of pentamethylvinyldisiloxane (yield amount: 5.0 g (13.0 mmol), yield amount: 59.7:6).

$^1$H-NMR (DMSO-$d_6$, 500 MHz, δ)
3.46 (s 6H), 2.41 (m, 2H), 1.87 (m, 2H), 1.56 (m, 4H), 0.13 (t, 3H), 0.77 (m, 4H), 0.30 (s, 12H).
$^{13}$C-NMR (DMSO-$d_6$, 125 Hz, δ)
55.0, 25.8, 25.2, 19.0, 17.7, 13.8, 0.5, 0.4.
$^{29}$Si-NMR (DMSO-$d_6$, 100 MHz, δ) 8.1, 7.7.

[Example 1-5] Synthesis of Sodium 2-[bis(trimethylsiloxy)methylsilyl]ethane-1-sulfonate (Me(Me$_3$SiO)$_2$SiC$_2$SO$_3$Na)

Me(Me$_3$SiO)$_2$SiC$_2$SO$_3$Na was obtained as a colorless solid (yield amount: 2.92 g (8.28 mmol), yield amount:

40.8%) in the same manner as in Example 1-1 except that 5.04 g 120.3 mmol of bis(trimethylsiloxy)(methyl)(vinyl) silane was used.

$^1$H-NMR (DMSO-d$_6$, 500 MHz, δ)

−0.01 (s, 3H), 0.07 (s, 18H), 0.77-0.81 (m 2H), 2.31-2.35 (m, 2H).

$^{13}$C NMR (DMSO-d$_6$, 125 Hz, δ) −0.4, 1.9, 13.2, 45.7.

[Example 2-1] Synthesis of tributyldodecylphosphonium 2-(1',1',3',3',3'-pentamethyl-disiloxanyl) ethane-1-sulfonate (BDDP MeSilC$_2$SO$_3$)

Figure 2:
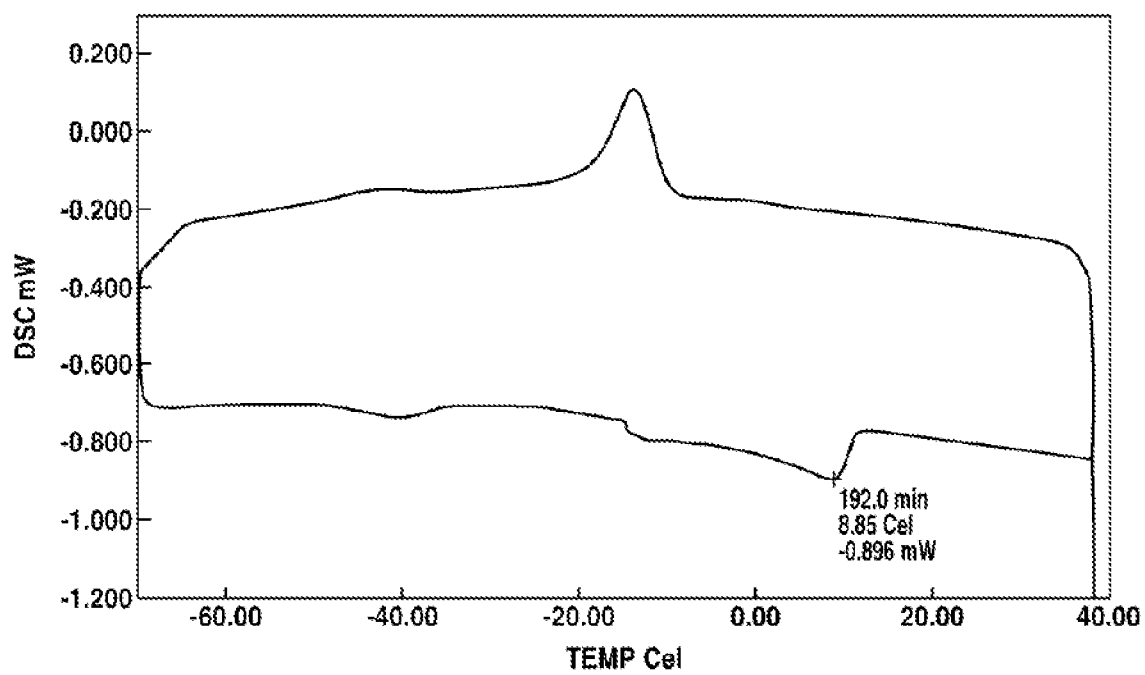
FIG. 2 is a DSC chart of BDDP MeSilC$_2$SO$_3$ prepared in Example 2-1.

An eggplant-shaped Schlenk flask equipped with a magnetic stirrer was degassed, and 1.02 g (3.05 mmol) of MeSilC$_2$SO$_3$Na and 25 mL of ion-exchanged water were charged into the flask under an argon stream, followed by stirring. When 2.67 g (3.28 mmol) of an aqueous solution of 50 wt % tributyldodecylphosphonium chloride was added thereto, the mixture became instantly cloudy. When the mixture was further stirred for 1 hour and then left to stand, the mixture was separated into two solution layers. An aqueous layer was removed, and ethyl acetate as an organic layer was extracted with ion-exchanged water several times. This was then dried over magnesium sulfate. After the dried product was concentrated with an evaporator, a solvent was distilled off under reduced pressure at 40 to 50° C. for 7 hours to obtain BDDP MeSilC$_2$SO$_3$ as a colorless transparent viscous liquid (yield amount: 1.68 g (2.46 mmol), yield: 80.6%). FIG. 1 shows a $^1$H-NMR spectrum, and FIG. 2 shows a DSC chart.

$^1$H-NMR (CDCl$_3$, 500 MHz, δ)

2.72 (m, 2H), 2.29 (m, 8H), 1.48 (m, 15H), 1.21 (m, 16H), 1.08 (m, 2H), 0.93 (t, 9H), 0.84 (t, 3H), 0.01 (s, 6H), 0.00 (s, 9H).

[Example 2-2] Synthesis of tributylhexadecylphosphonium 2-(1',1',3',3',3'-pentamethyl-disiloxanyl) ethane-1-sulfonate (BHDP MeSilC$_2$SO$_3$)

Figure 3:
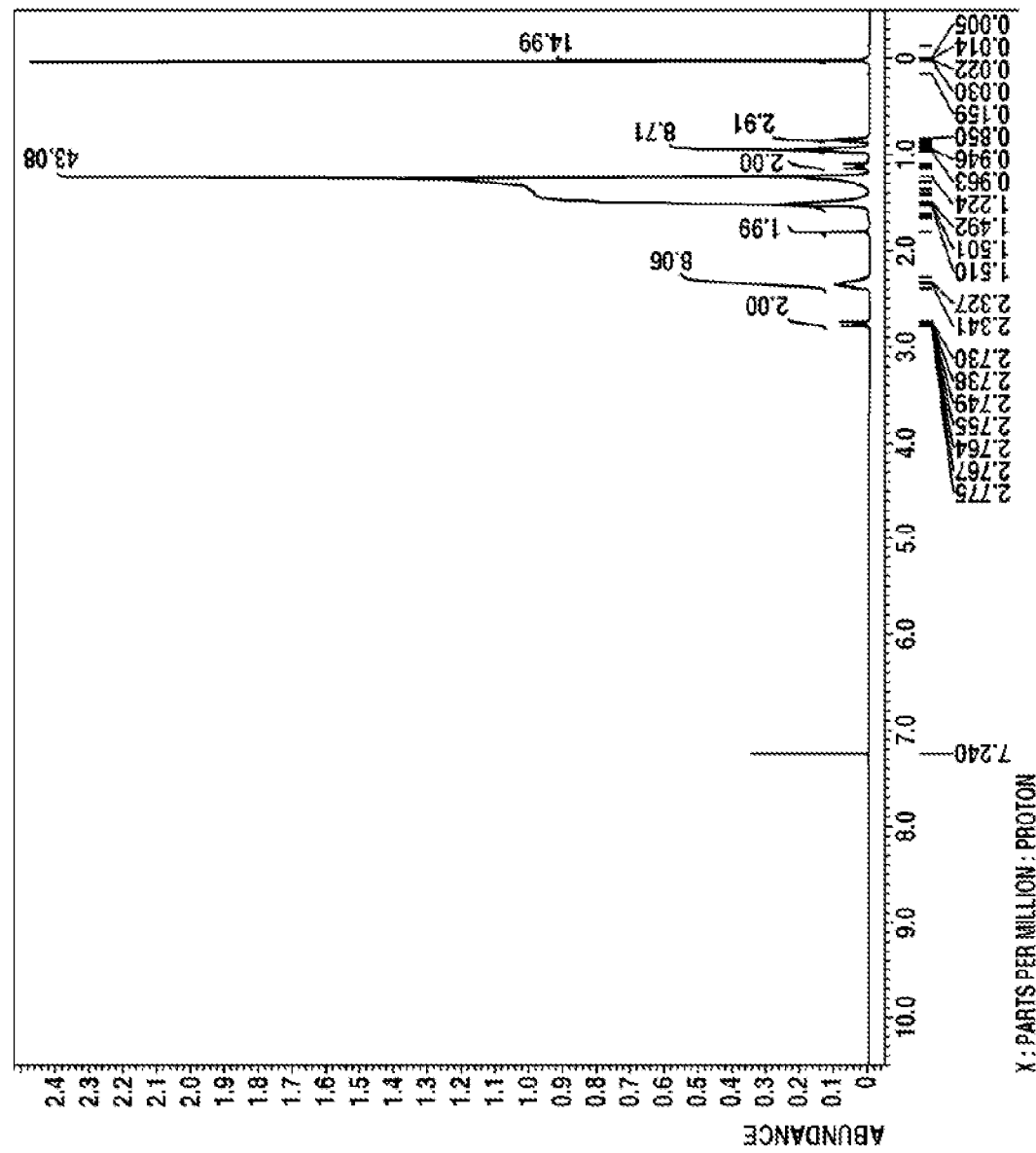
FIG. 3 is a $^1$H-NMR spectrum of BHDP MeSilC$_2$SO$_3$ prepared in Example 2-2.
Figure 4:
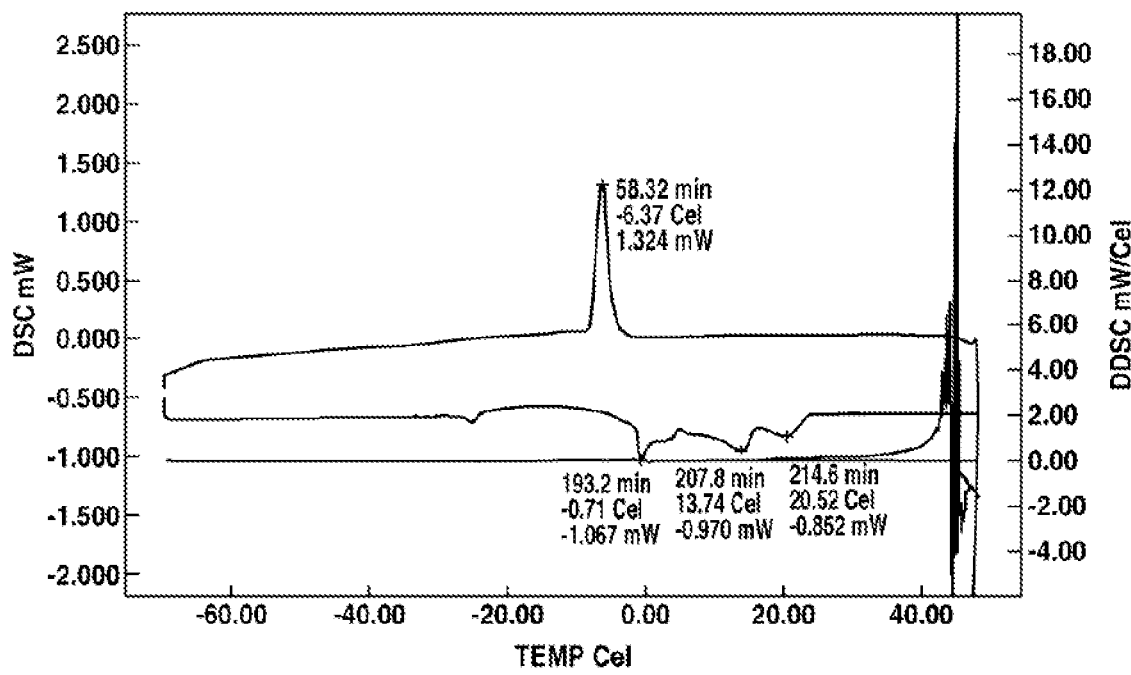
FIG. 4 is a DSC chart of BHDP MeSilC$_2$SO$_3$ prepared in Example 2-2.

BHDP MeSilC$_2$SO$_3$ was obtained as a colorless transparent viscous liquid (yield amount: 1.66 g (2.43 mmol), yield: 77.6%) in the same manner as in Example 2-1 except that the amount of MeSilC$_2$SO$_3$Na used was 1.04 g (3.13 mmol), the amount of ion-exchanged water used was 20 mL; and 2.99 g (3.22 mmol) of an aqueous solution of 50 wt % tributylhexadecylphosphonium chloride was used in place of an aqueous solution of 50 wt % tributyldodecylphosphonium chloride. FIG. 3 shows a $^1$H-NMR spectrum, and FIG. 4 shows a DSC chart.

[Example 2-3] Synthesis of tributyldodecylphosphonium 3-(1',1',3',3',3'-pentamethyl-disiloxanyl) propane-1-sulfonate (BDDP MeSilC$_3$SO$_3$)

Figure 5:
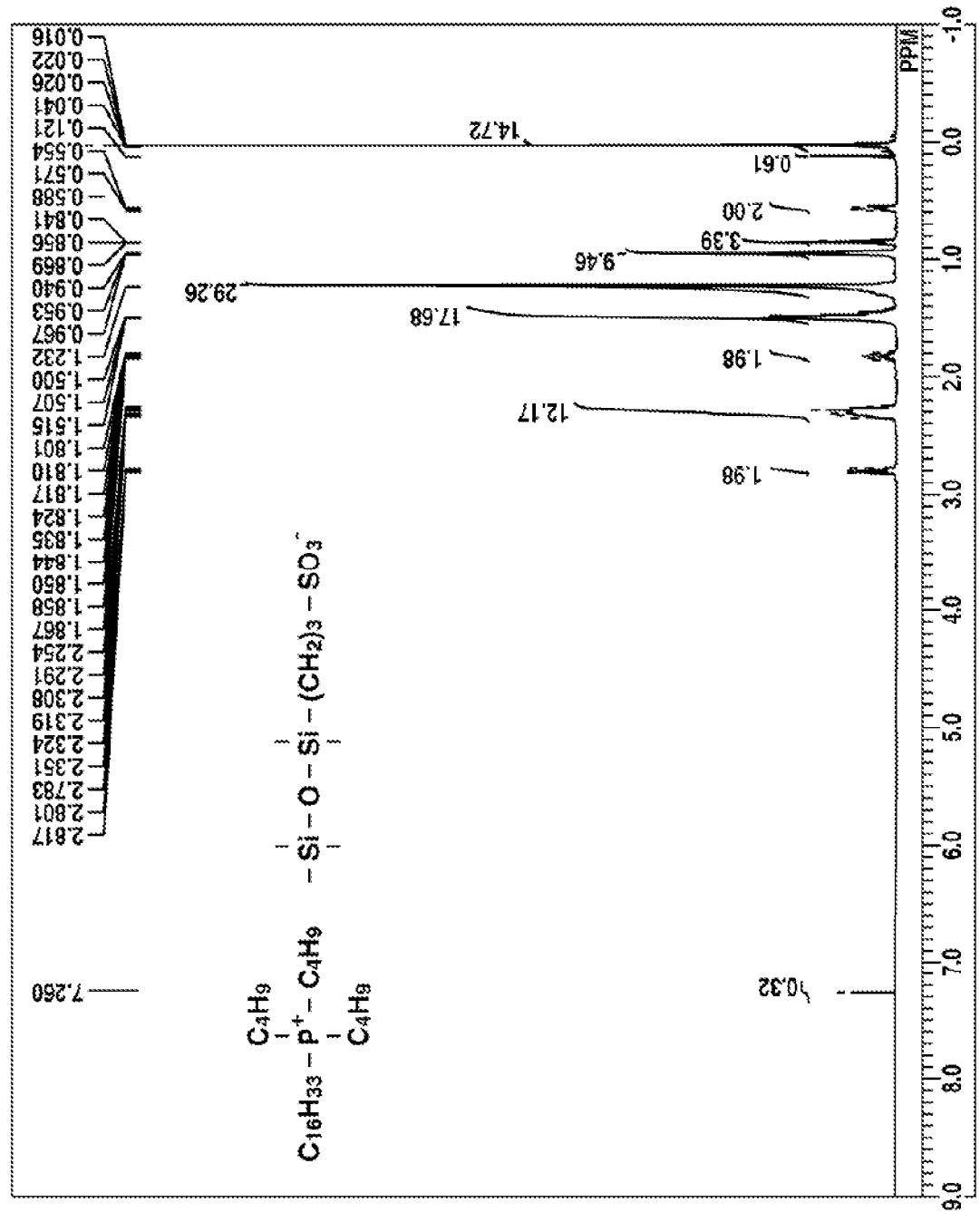
FIG. 5 is a $^1$H-NMR spectrum of BDDP MeSilC$_3$SO$_3$ prepared in Example 2-3.
Figure 6:
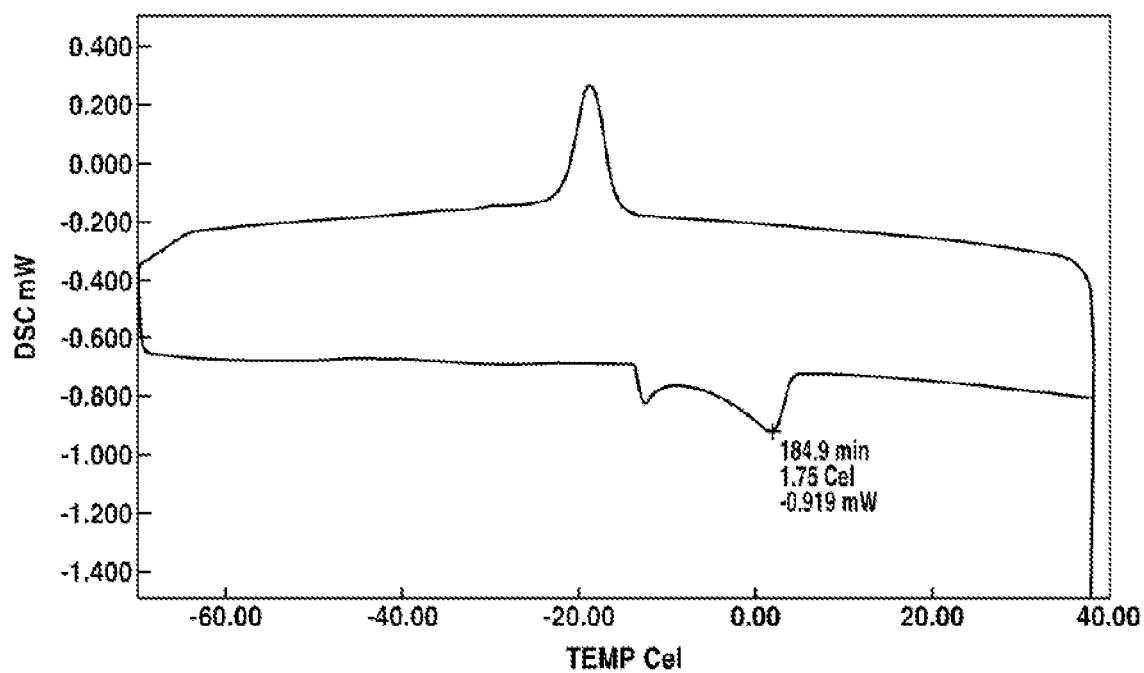
FIG. 6 is a DSC chart of BDDP MeSilC$_3$SO$_3$ prepared in Example 2-3.

BDDP MeSilC$_3$SO$_3$ was obtained as a colorless transparent viscous liquid (yield amount: 0.43 g (0.68 mmol), yield: 47.2%) in the same manner as in Example 2-1 except that 0.52 g (1.42 mmol) of MeSilC$_3$SO$_3$Na was used in place of MeSilC$_2$SO$_3$Na; the amount of ion-exchanged water used was 5 mL; and the amount of an aqueous solution of 50 wt % tributyldodecylphosphonium chloride used was 1.31 g (1.61 mmol). FIG. 5 shows a $^1$H-NMR spectrum, and FIG. 6 shows a DSC chart.

$^1$H-NMR (CDCl$_3$, 500 MHz, δ)

2.80 (m, 2H), 2.32 (m, 8H), 1.84 (m, 2H), 1.50 (m, 16H), 1.23 (m, 14H), 0.95 (t, 9H), 0.85 (t, 3H), 0.56 (m, 2H), 0.02 (s, 15H).

$^{13}$C-NMR (CDCl$_3$, 125 MHz, δ)

56.0, 32.1, 31.0 (d, J=15.5 Hz), 29.8, 29.7, 29.5, 29.2, 24.2 (d, J=15.5 Hz), 24.0 (d, J=4.8 Hz), 22.8, 22.1 (d, J=4.8 Hz), 19.6, 19.2 (d, J=46.5 Hz), 19.0 (J=46.5 Hz), 18.3, 14.3, 13.7, 2.2, 0.5.

[Example 2-4] Synthesis of tributylhexadecylphosphonium 3-(1',1',3',3',3'-pentamethyl-disiloxanyl) propane-1-sulfonate (BHDP MeSilC$_3$SO$_3$)

Figure 7:
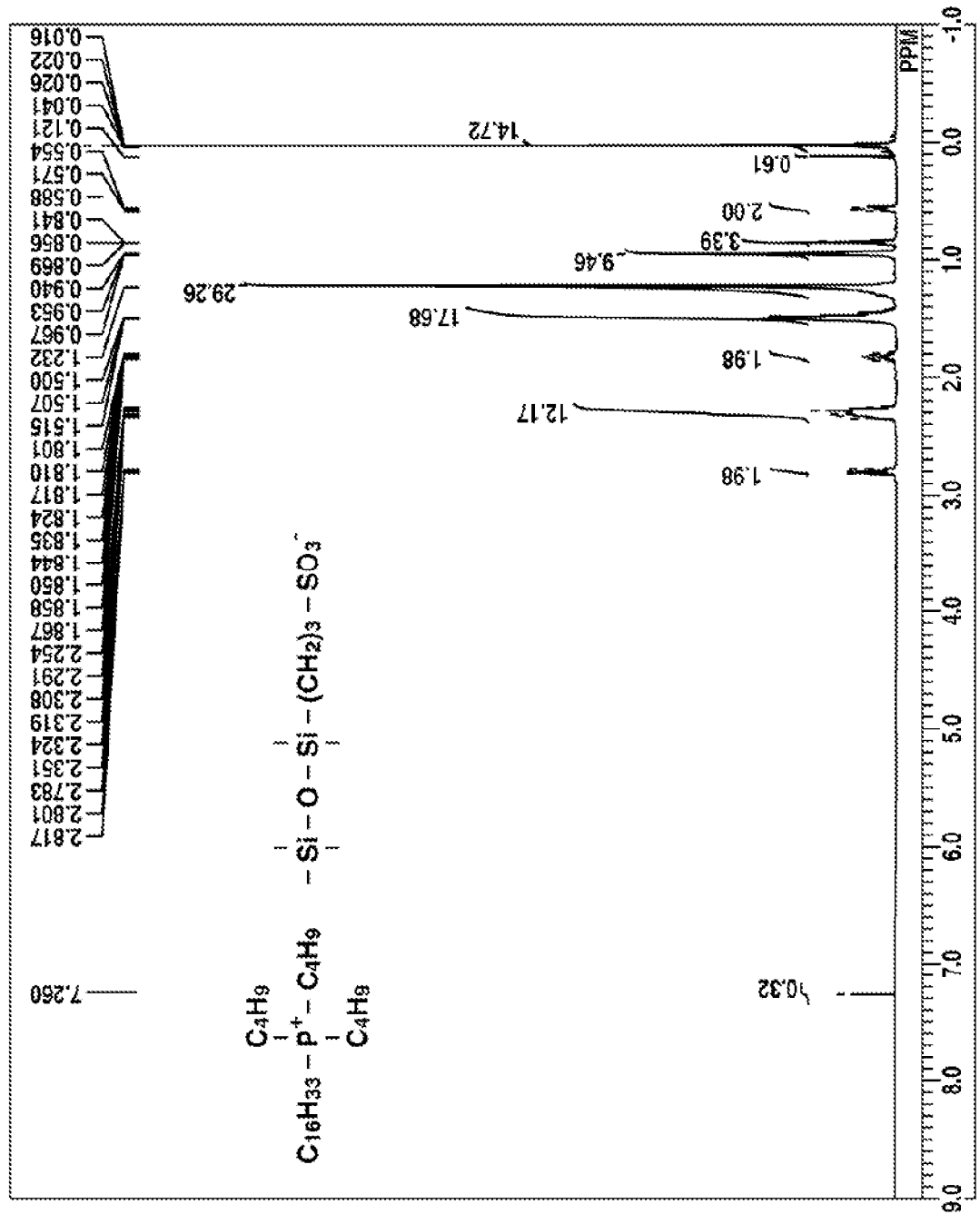
FIG. 7 is a $^1$H-NMR spectrum of BHDP MeSilC$_3$SO$_3$ prepared in Example 2-4.
Figure 8:
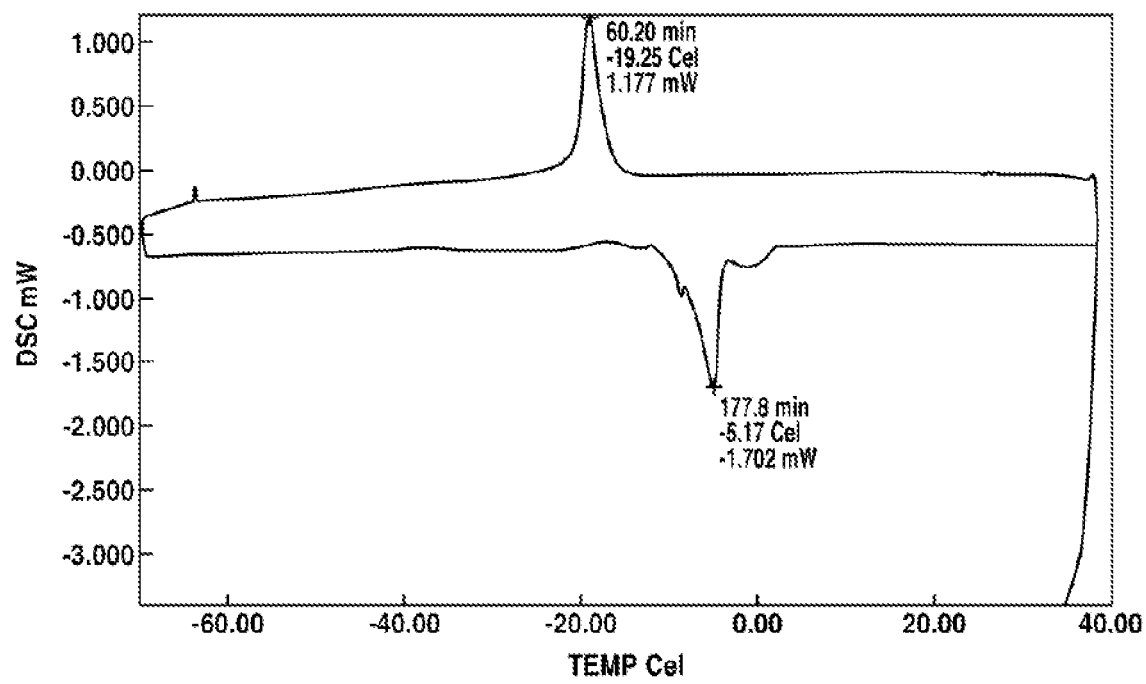
FIG. 8 is a DSC chart of BHDP MeSilC$_3$SO$_3$ prepared in Example 2-4.

BHDP MeSilC$_3$SO$_3$ was obtained as a colorless transparent viscous liquid (yield amount: 0.15 g (0.22 mmol), yield: 15.3%) in the same manner as in Example 2-2 except that 0.52 g (1.42 mmol) of MeSilC$_3$SO$_3$Na was used in place of MeSilC$_2$SO$_3$Na; the amount of ion-exchanged water used was 5 mL; and the amount of an aqueous solution of 50 wt % tributylhexadecylphosphonium chloride used was 1.45 g (1.56 mmol). FIG. 7 shows a $^1$H-NMR spectrum, and FIG. 8 shows a DSC chart.

[Example 2-5] Synthesis of tributyldodecylphosphonium 2-(3'-n-butyl-1',1',3',3'-tetramethyldisiloxanyl) ethane-1-sulfonate (BDDP BuSilC$_2$SO$_3$)

Figure 9:
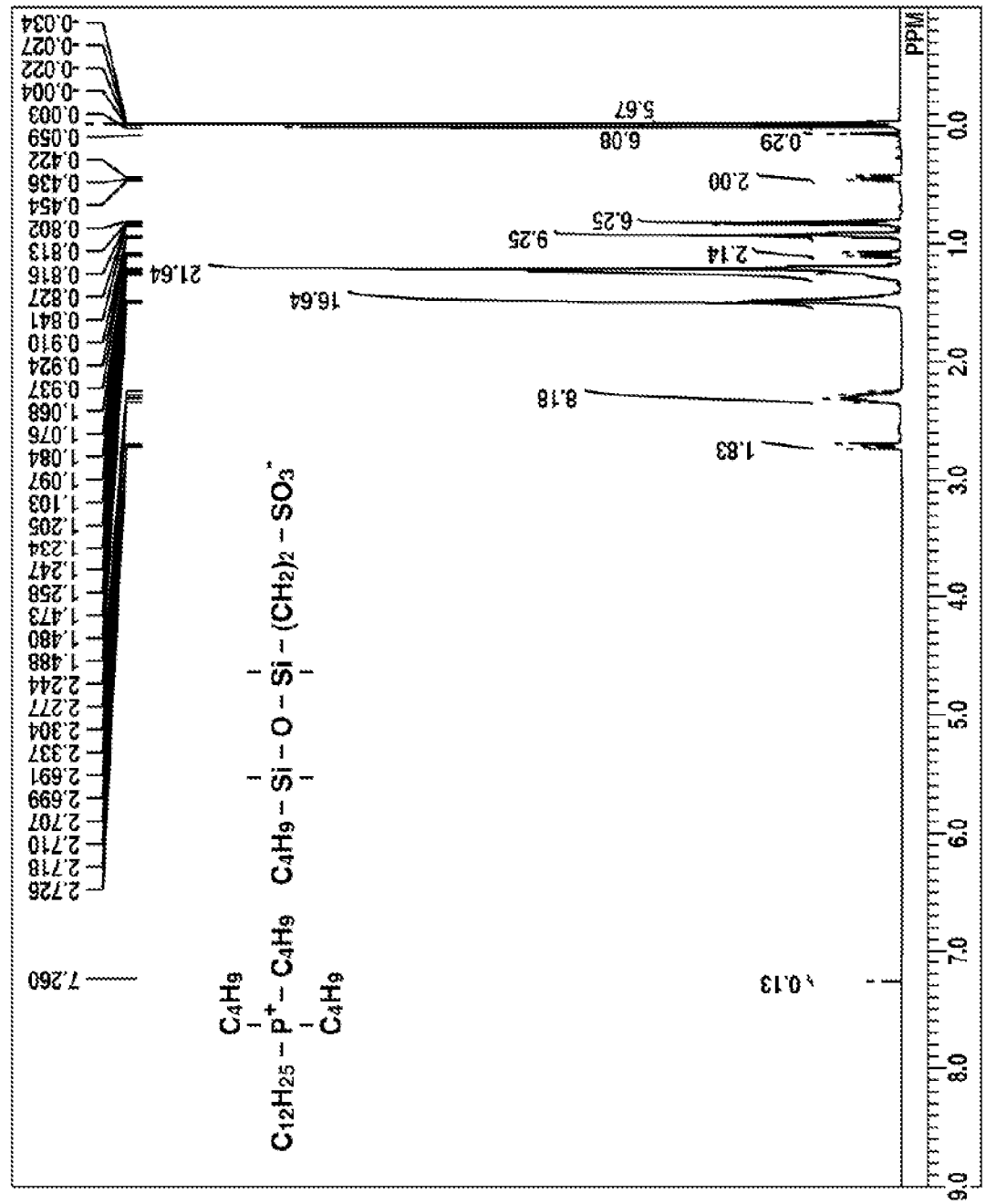
FIG. 9 is a $^1$H-NMR spectrum of BDDP BuSilC$_2$SO$_3$ prepared in Example 2-5.
Figure 10:
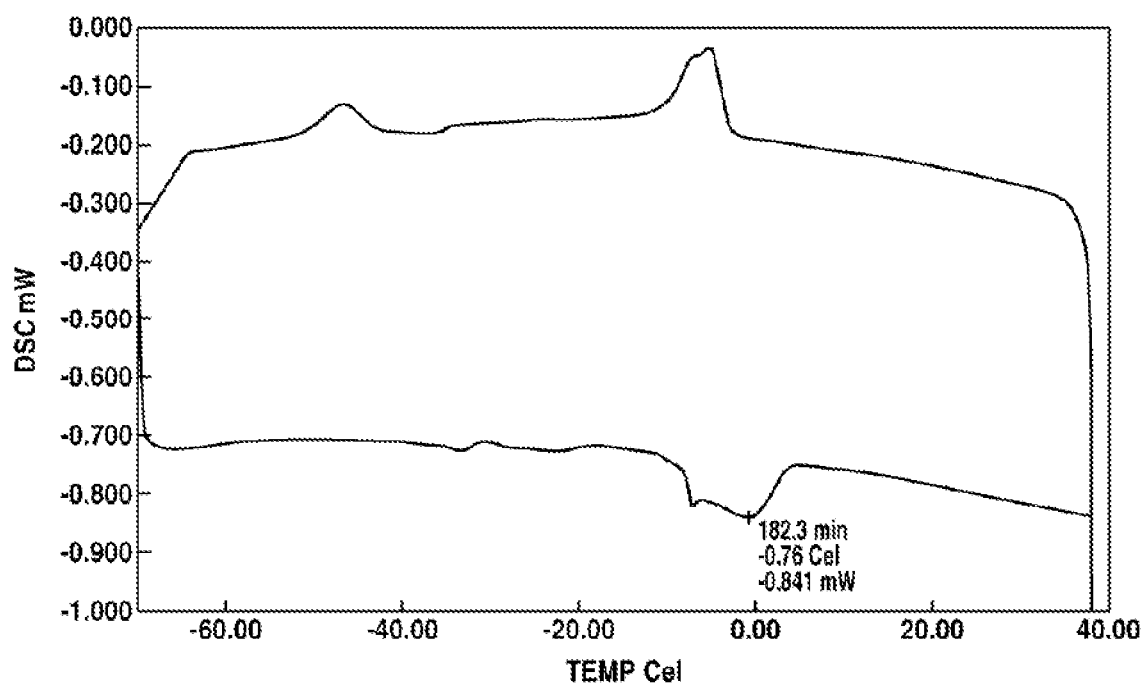
FIG. 10 is a DSC chart of BDDP BuSilC$_2$SO$_3$ prepared in Example 2-5.

BDDP BuSilC$_2$SO$_3$ was obtained as a colorless transparent viscous liquid (yield amount: 0.33 g (0.48 mmol), yield: 33.3%) in the same manner as in Example 2-1 except that 0.51 g (1.44 mmol) of BuSilC$_2$SO$_3$Na was used in place of MeSilC$_2$SO$_3$Na; the amount of ion-exchanged water used was 10 mL; and the amount of an aqueous solution of 50 wt % tributyldodecylphosphonium chloride used was 1.23 g (1.51 mmol). FIG. 9 shows a $^1$H-NMR spectrum, and FIG. 10 shows a DSC chart.

[Example 2-6] Synthesis of tributylhexadecylphosphonium 2-(3'-n-butyl-1',1',3',3'-tetramethyldisiloxanyl)ethane-1-sulfonate (BHDP BuSilC$_2$SO$_3$)

Figure 11:
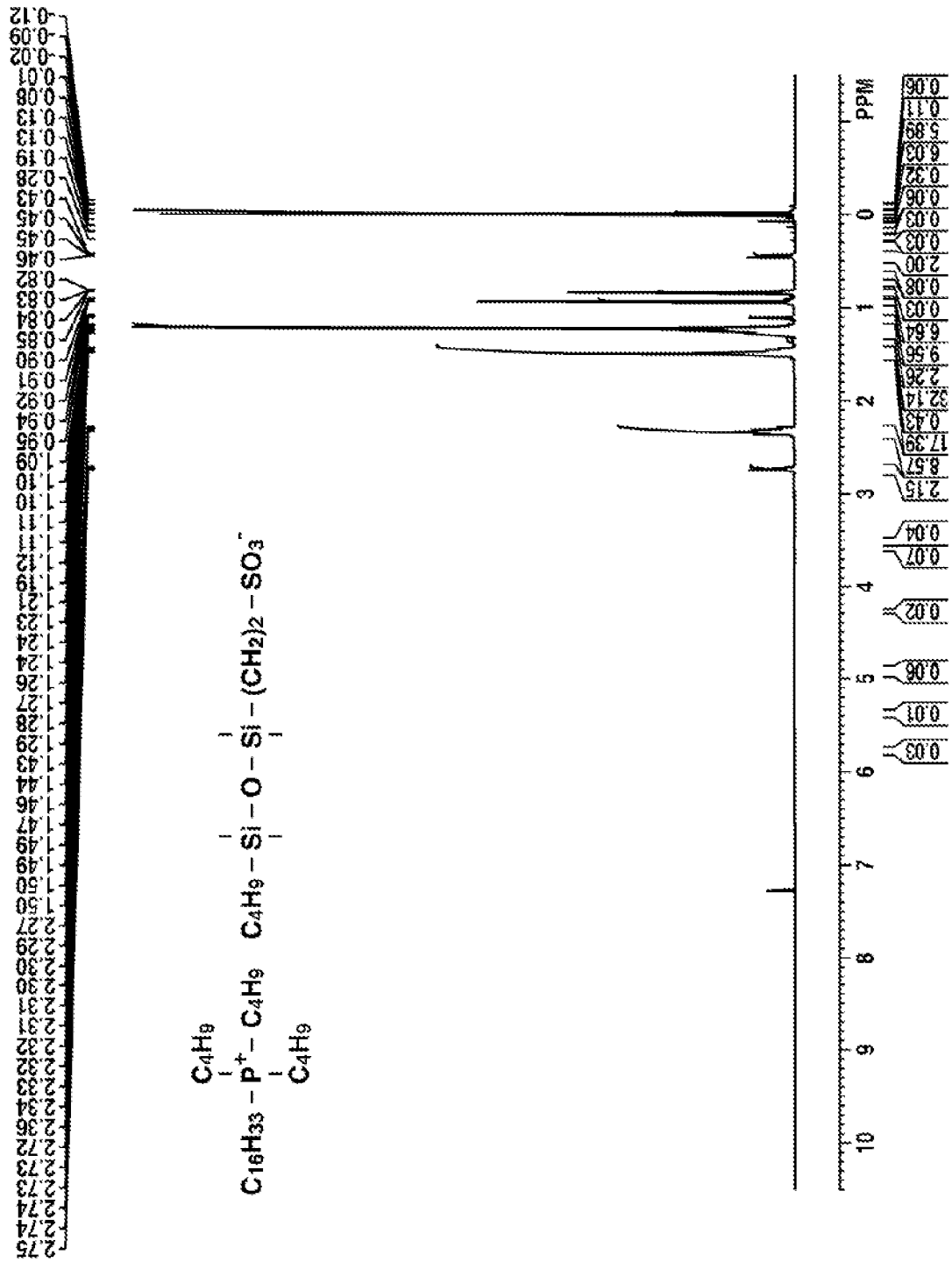
FIG. 11 is a $^1$H-NMR spectrum of BHDP BuSilC$_2$SO$_3$ prepared in Example 2-6.
Figure 12:
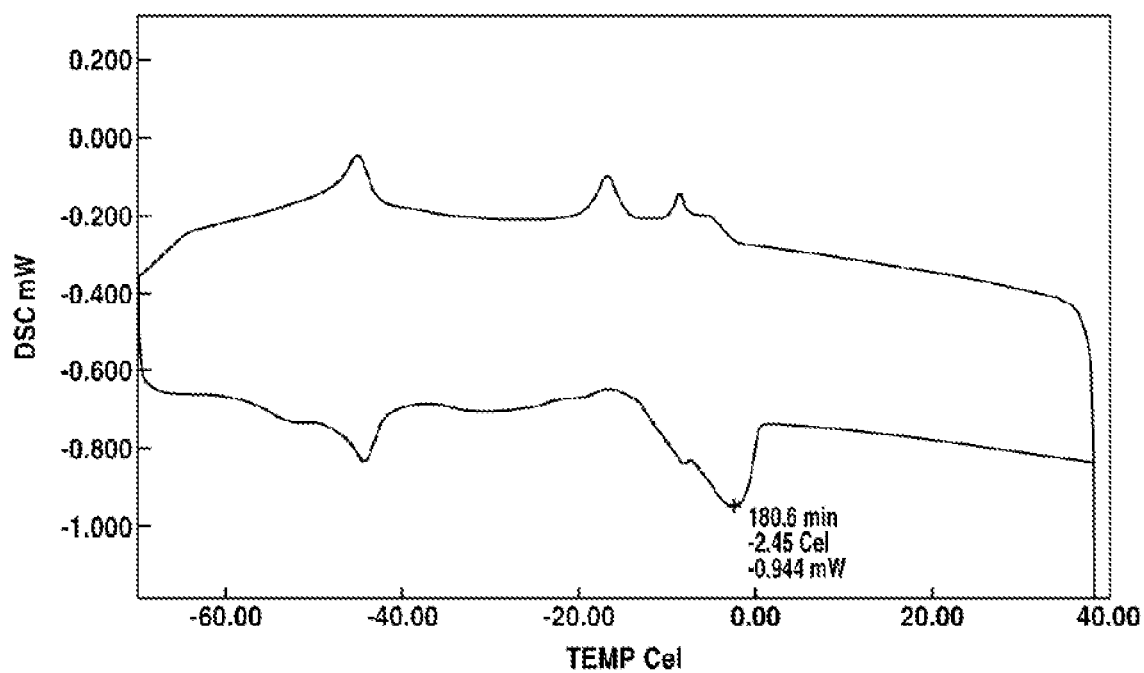
FIG. 12 is a DSC chart of BHDP BuSilC$_2$SO$_3$ prepared in Example 2-6.

BHDP BuSilC$_2$SO$_3$ was obtained as a colorless transparent viscous liquid (yield amount: 0.64 g (0.88 mmol), yield: 54.3%) in the same manner as in Example 2-2 except that 0.60 g (1.62 mmol) of BuSilC$_2$SO$_3$Na was used in place of MeSilC$_2$SO$_3$Na: the amount of ion-exchanged water used was 10 mL; and the amount of an aqueous solution of 50 wt % tributylhexadecylphosphonium chloride used was 1.59 g (1.72 mmol). FIG. 11 shows a $^1$H-NMR spectrum and FIG. 12 shows a DSC chart.

[Example 2-7] Synthesis of tributyldodecylphosphonium 3-(3'-n-butyl-1',1',3',3'-tetramethyldisiloxanyl)propane-1-sulfonate (BDDP BuSilC$_3$SO$_3$)

Figure 13:
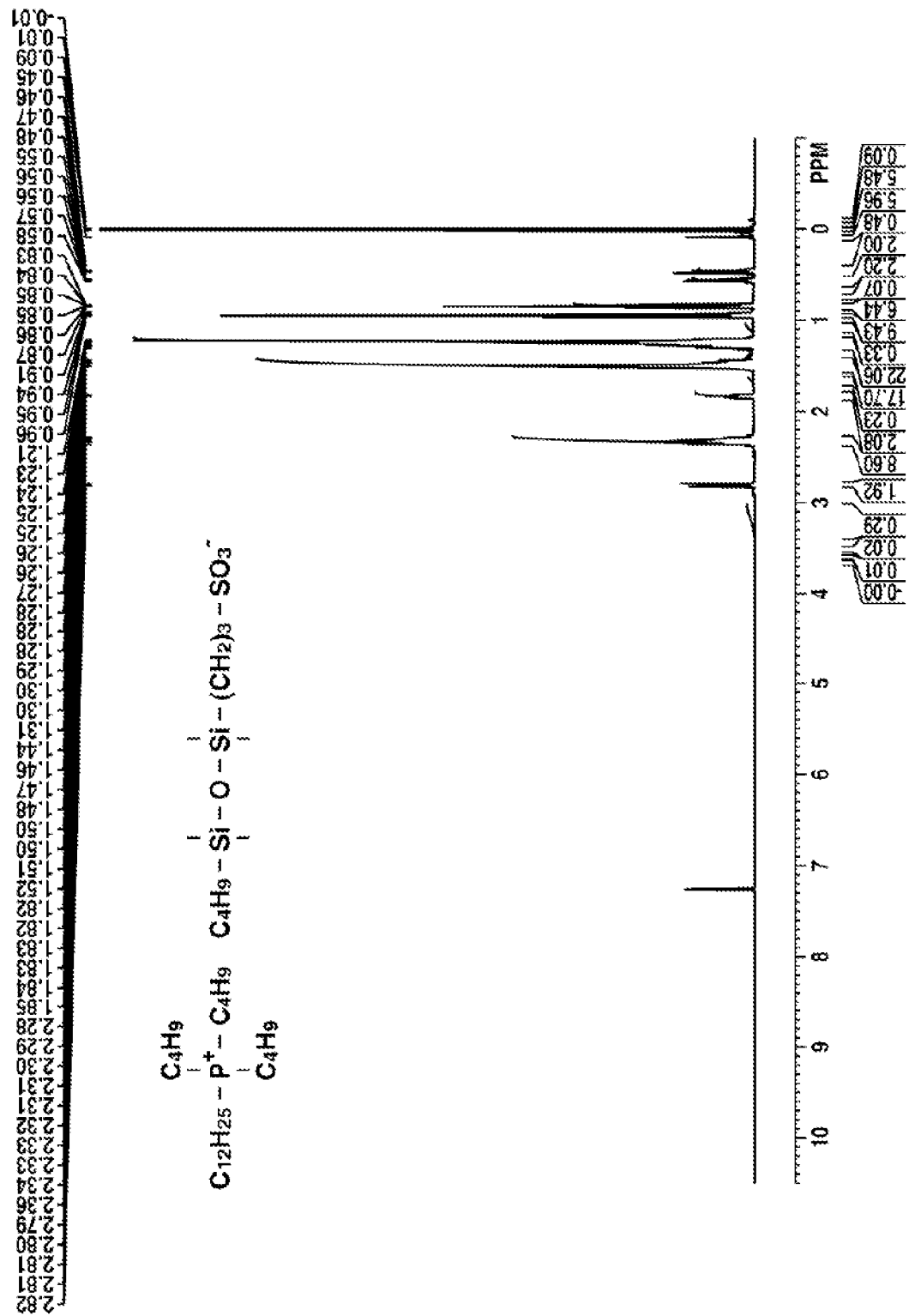
FIG. 13 is a $^1$H-NMR spectrum of BDDP BuSilC$_3$SO$_3$ prepared in Example 2-7.
Figure 14:
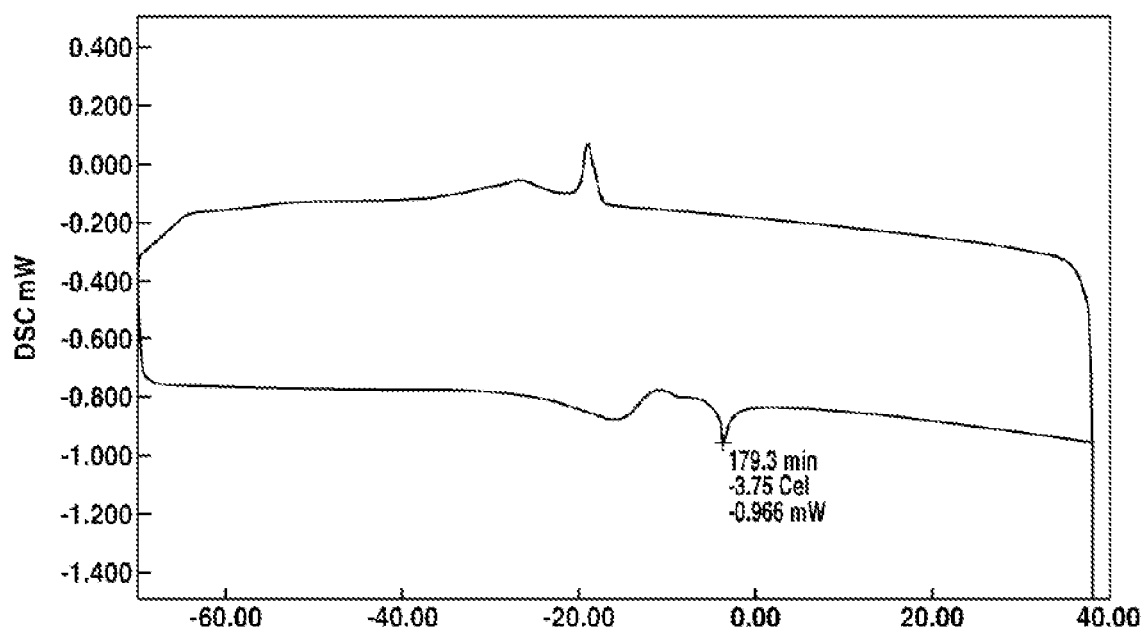
FIG. 14 is a DSC chart of BDDP BuSilC$_3$SO$_3$ prepared in Example 2-7.

BDDP BuSilC$_3$SO$_3$ was obtained as a colorless transparent viscous liquid (yield amount: 0.71 g (1.06 mmol), yield: 42.0%) in the same manner as in Example 2-1 except that 1.03 g (2.52 mmol) of BuSilC$_3$SO$_3$Na was used in place of MeSilC$_2$SO$_3$Na; the amount of ion-exchanged water used was 10 mL; and the amount of an aqueous solution of 50 wt % tributyldodecylphosphonium chloride used was 2.22 g (2.73 mmol). FIG. 13 shows a $^1$H-NMR spectrum, and FIG. 14 shows a DSC chart.

[Example 2-8] Synthesis of tributylhexadecylphosphonium 3-(3'-n-butyl-1'1',3',3'-tetramethyldisiloxanyl)propane-1-sulfonate (BHDP BuSilC$_3$SO$_3$)

Figure 15:
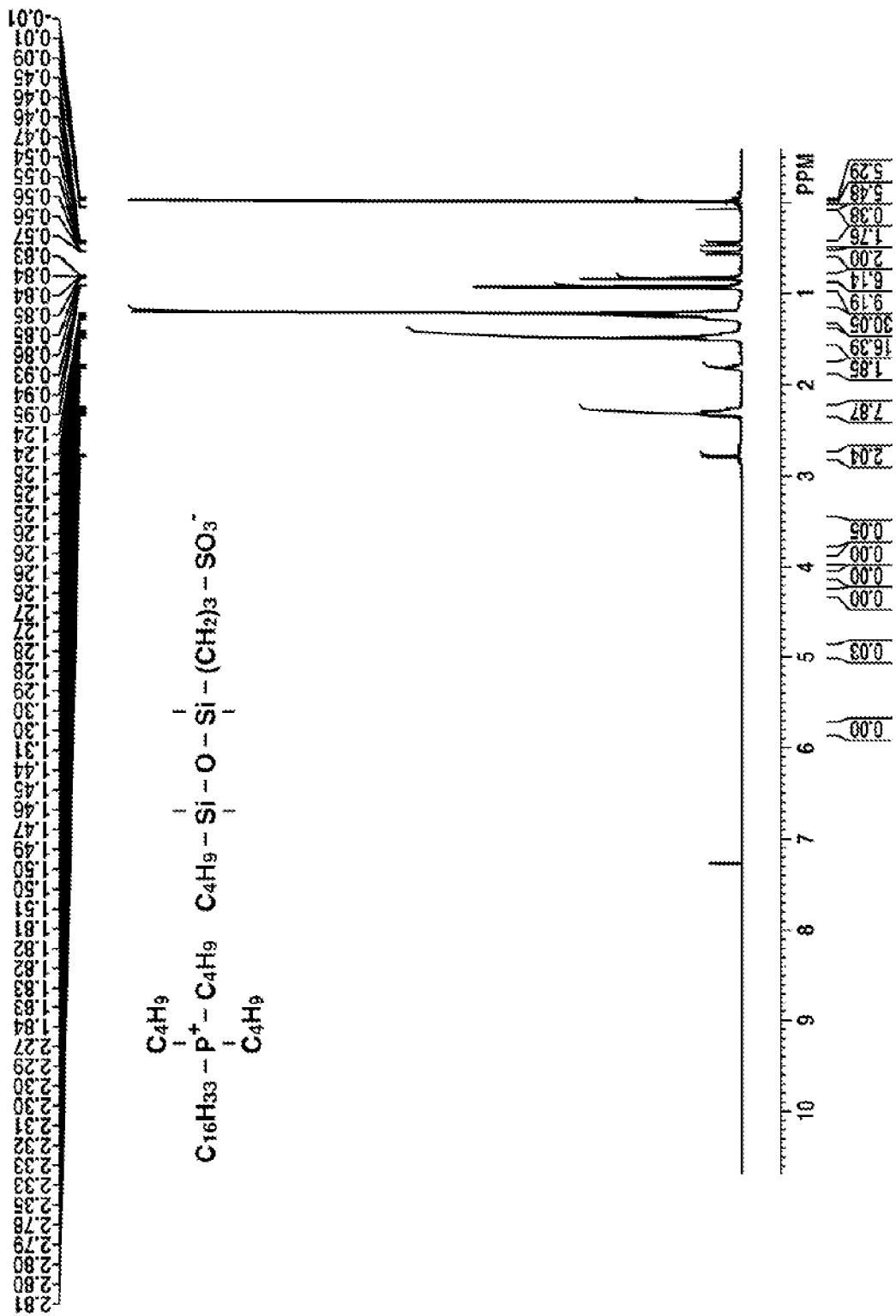
FIG. 15 is a $^1$H-NMR spectrum of BHDP BuSilC$_3$SO$_3$ prepared in Example 2-8.
Figure 16:
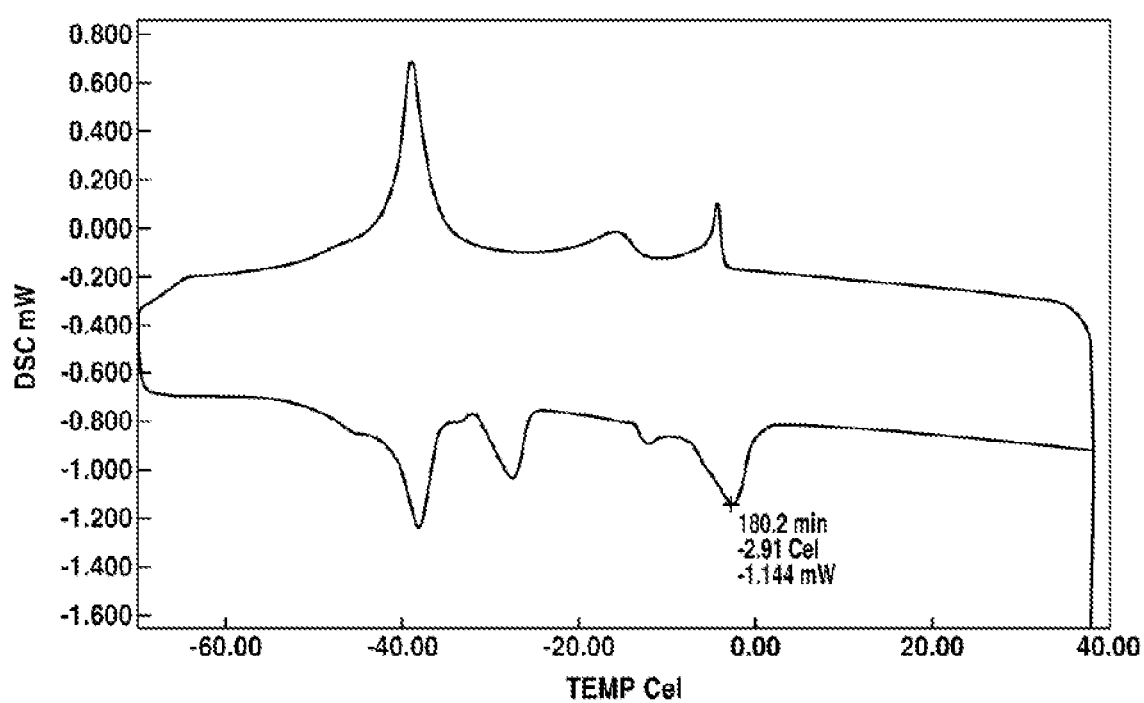
FIG. 16 is a DSC chart of BHDP BuSilC$_3$SO$_3$ prepared in Example 2-8.

BHDP BuSilC$_3$SO$_3$ was obtained as a colorless transparent viscous liquid (yield amount: 0.75 g (1.01 mmol), yield: 69.1%) in the same manner as in Example 2-2 except that 0.51 g (1.46 mmol) of BuSilC$_3$SO$_3$Na was used in place of MeSilC$_2$SO$_3$Na; the amount of ion-exchanged water used was 10 mL; and the amount of an aqueous solution of 50 wt % tributylhexadecylphosphonium chloride used was 1.36 g (1.47 mmol). FIG. 15 shows a $^1$H-NMR spectrum, and FIG. 16 shows a DSC chart.

[Example 2-9] Synthesis of tributyldodecylphosphonium 2-[bis(trimethylsiloxy)-methylsilyl]ethane-1-sulfonate (BDDP Me(Me$_3$SiO)$_2$SiC$_2$SO$_3$)

Figure 17:
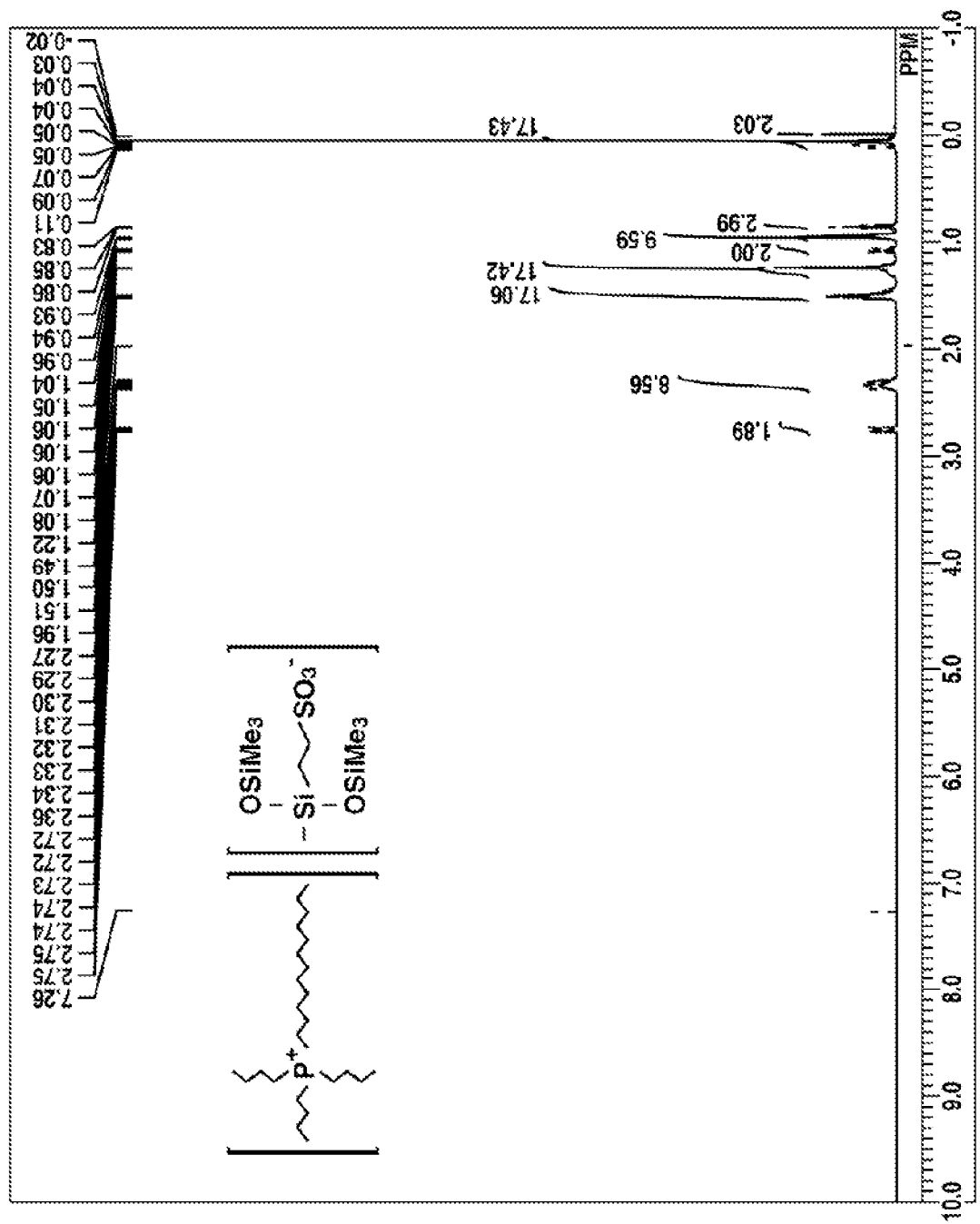
FIG. 17 is a $^1$H-NMR spectrum of BDDP Me(Me$_3$SiO)$_2$SiC$_2$SO$_3$ prepared in Example 2-9.
Figure 18:
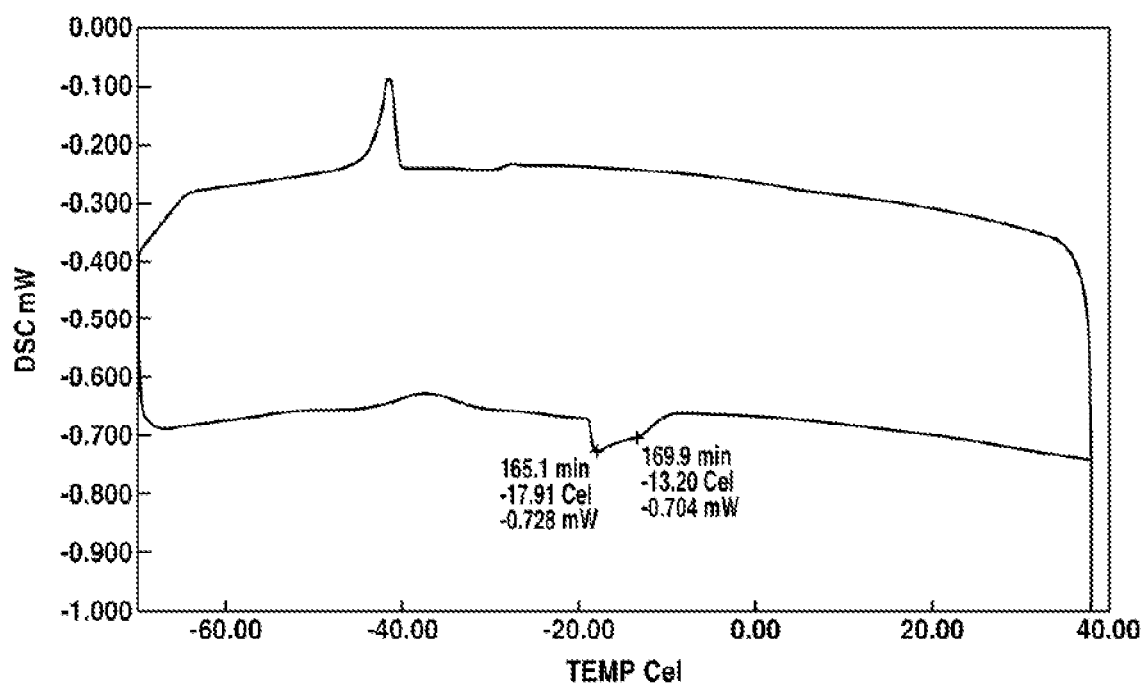
FIG. 18 is a DSC chart of BDDP Me(Me$_3$SiO)$_2$SiC$_2$SO$_3$ prepared in Example 2-9.

BDDP Me(Me$_3$SiO)$_2$SiC$_2$SO$_3$ was obtained as a colorless transparent viscous liquid (yield amount: 0.40 g (0.57 mmol), yield: 45.5%) in the same manner as in Example 2-1 except that 0.53 g (1.25 mmol) of Me(Me$_3$SiO)SiC$_2$SO$_3$Na was used instead of MeSilC$_2$SO$_3$Na; the amount of ion-exchanged water used was 10 mL; and the amount of an aqueous solution of 50 wt % tributyldodecylphosphonium chloride used was 1.06 g (1.30 mmol). FIG. 17 shows a $^1$H-NMR spectrum, and FIG. 18 shows a DSC chart.

[Example 2-10] Synthesis of tributylhexadecylphosphonium 2-[bis(trimethylsiloxy)-methylsilyl]ethane-1-sulfonate (BHDP Me(Me$_3$SiO)$_2$SiC$_2$SO$_3$)

Figure 19:
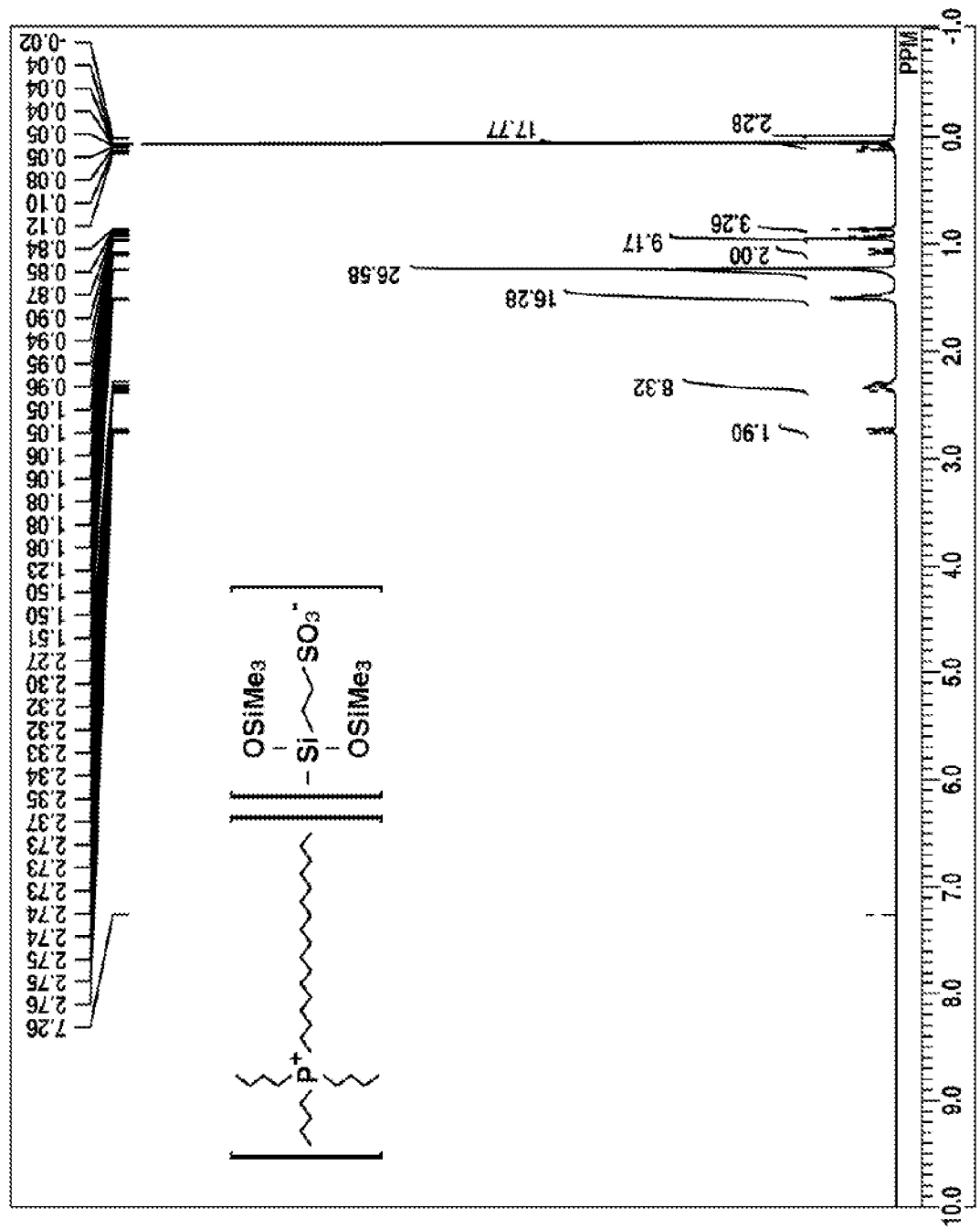
FIG. 19 is a $^1$H-NMR spectrum of BHDP Me(Me$_3$SiO)$_2$SiC$_2$SO$_3$ prepared in Example 2-10.
Figure 20:
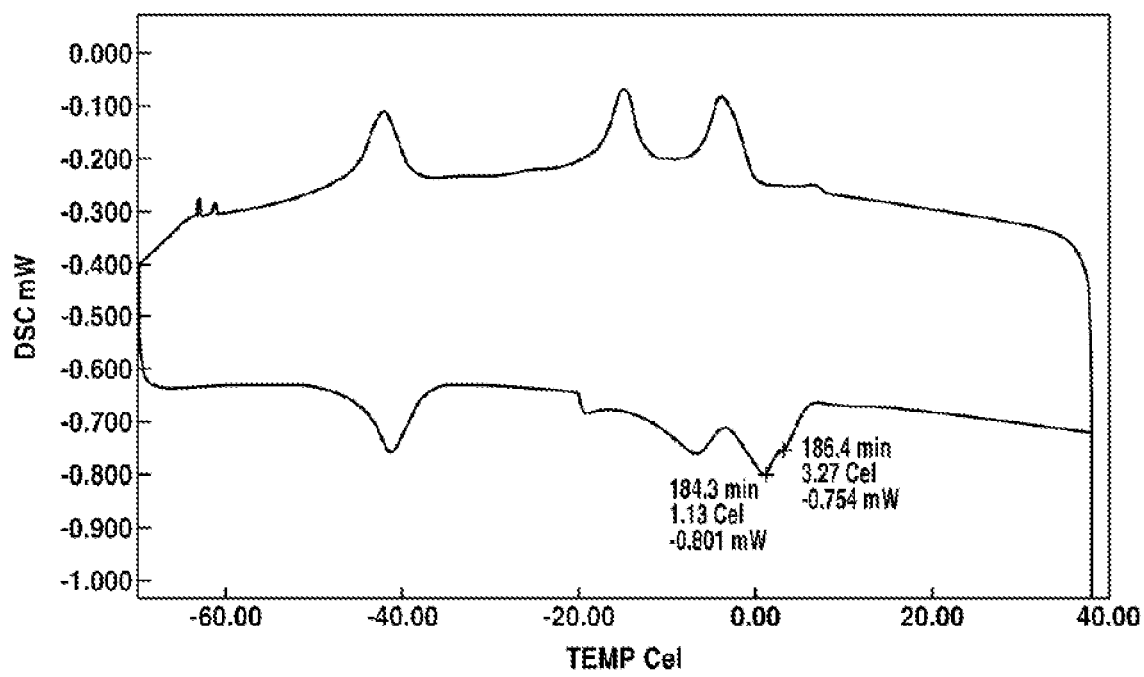
FIG. 20 is a DSC chart of BHDP Me(Me$_3$SiO)$_2$SiC$_2$SO$_3$ prepared in Example 2-10.

BHDP Me(Me$_3$SiO)$_2$SiC$_2$SO$_3$ was obtained as a colorless transparent viscous liquid (yield amount: 0.48 g (0.63 mmol), yield: 27.0%) in the same manner as in Example 2-2 except that 1.00 g (2.34 mmol) of Me(Me$_3$SiO)$_2$SiC$_2$SO$_3$Na was used instead of MeSilC$_2$SO$_3$Na; the amount of ion-exchanged water used was 18 and the amount of an aqueous solution of 50 wt % tributylhexadecylphosphonium chloride used was 2.20 g (2.37 mmol). FIG. 19 shows a $^1$H-NMR spectrum, and FIG. 20 shows a DSC chart.

[Example 2-11] Synthesis of 2-(1',1',3',3',3'-pentamethyldisiloxanyl)ethane-1-sulfonate N-2-methoxyethyl-N-methylpyrrolidinium (MEMP MeSilC$_2$SO$_3$)

Figure 21:
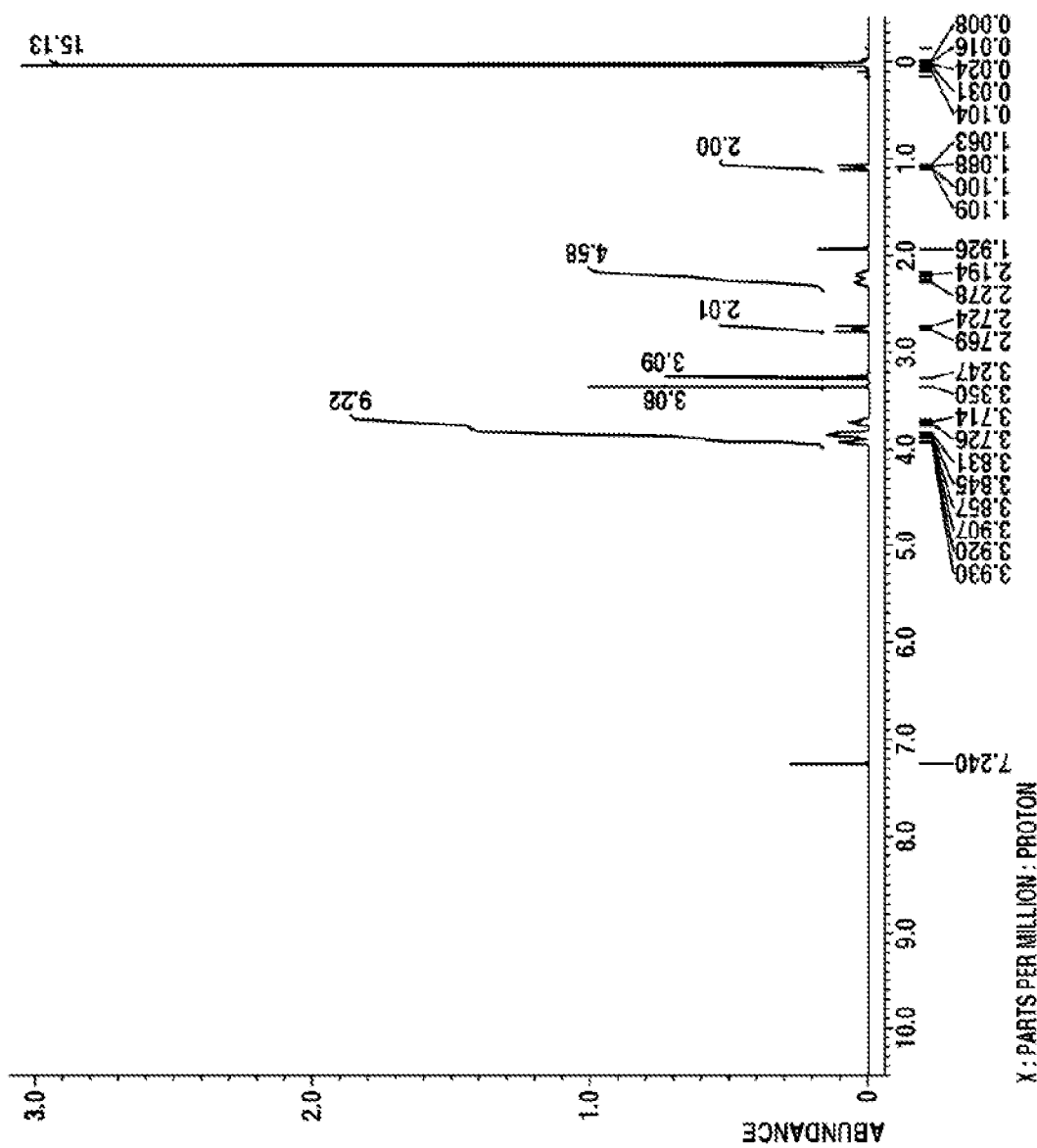
FIG. 21 is a $^1$H-NMR spectrum of MEMP MeSilC$_2$SO$_3$ prepared in Example 2-11.
Figure 22:
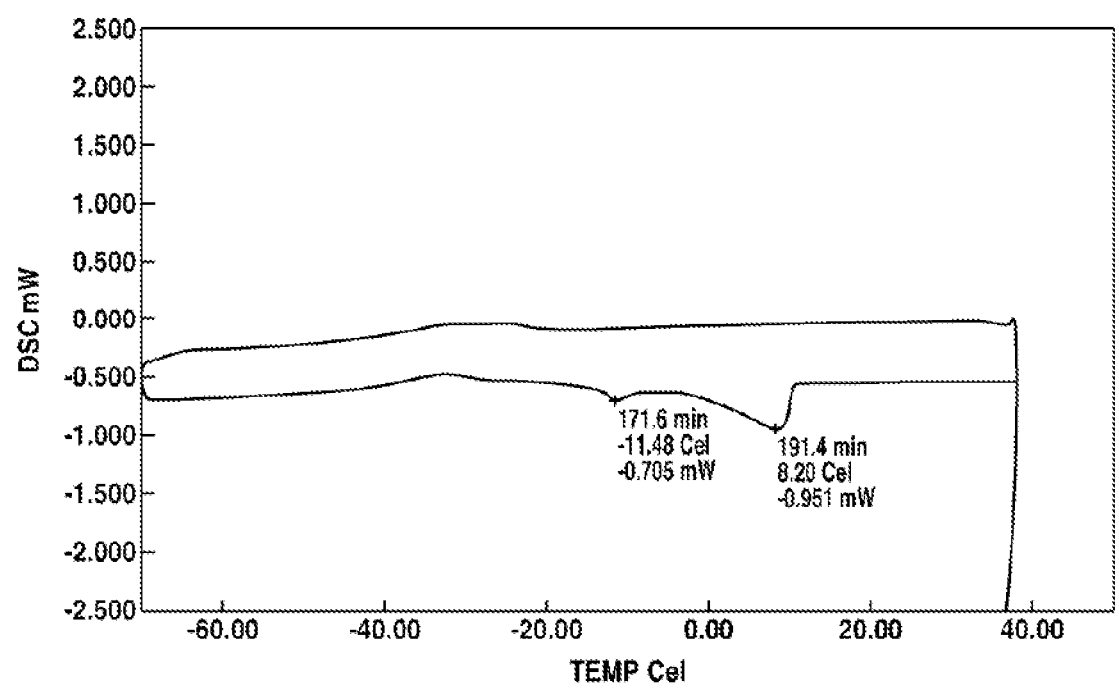
FIG. 22 is a DSC chart of MEMP MeSilC$_2$SO$_3$ prepared in Example 2-11.

Into an eggplant-shaped flask equipped with a magnetic stirrer, 1.17 g (4.20 mmol) of MeSilC$_2$SO$_3$Na and 10 mL of acetonitrile were charged, followed by stirring. 0.67 g (3.82 mmol) of N-2-methoxyethyl-N-methylpyrrolidinium chloride dissolved in 2 mL of acetonitrile was added thereto. After stirring overnight, the precipitate was filtered off. The filtrate was concentrated with an evaporator followed by a vacuum pump to obtain a desired product, MEMP MeSilC$_2$SO$_3$, as a colorless transparent viscous liquid (yield amount: 1.52 g (3.80 mmol), yield: 99.5%). FIG. 21 shows a $^1$H-NMR spectrum, and FIG. 22 shows a DSC chart.

The melting point and shape at 25° C. of each silyl ether-containing sulfonate salt obtained by DSC measurement are shown in Table 1.

TABLE 1

| Example | | Melting point (° C.) | Shape |
|---|---|---|---|
| 2-1 | BDDP MeSilC$_2$SO$_3$ | 9° C. | Colorless transparent viscous liquid |
| 2-2 | BHDP MeSilC$_2$SO$_3$ | 21° C. | Colorless transparent viscous liquid |
| 2-3 | BDDP MeSilC$_3$SO$_3$ | 2° C. | Colorless transparent viscous liquid |
| 2-4 | BHDP MeSilC$_3$SO$_3$ | −5° C. | Colorless transparent viscous liquid |
| 2-5 | BDDP BuSilC$_2$SO$_3$ | −1° C. | Colorless transparent viscous liquid |
| 2-6 | BHDP BuSilC$_2$SO$_3$ | −2° C. | Colorless transparent viscous liquid |
| 2-7 | BDDP BuSilC$_3$SO$_3$ | −4° C. | Colorless transparent viscous liquid |
| 2-8 | BHDP BuSilC$_3$SO$_3$ | −3° C. | Colorless transparent viscous liquid |
| 2-9 | BDDP Me(Me$_3$SiO)$_2$SiC$_2$SO$_3$ | −13° C. | Colorless transparent viscous liquid |
| 2-10 | BHDP Me(Me$_3$SiO)$_2$SiC$_2$SO$_3$ | 3° C. | Colorless transparent viscous liquid |
| 2-11 | MEMP MeSilC$_2$SO$_3$ | 8° C. | Colorless transparent viscous liquid |

The invention claimed is:

1. A silyl ether-containing sulfonate salt comprising:
an anion having the following formula (1); and
an organic cation which is a phosphorus atom-containing organic cation or a nitrogen atom containing organic cation,

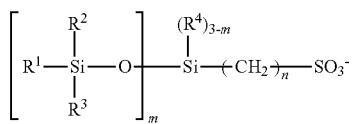
(1)

wherein:
$R^1$ to $R^4$ are each independently an alkyl group having 1 to 4 carbon atoms;
m is an integer of 1 to 3; and
n is an integer of 2 to 8, and
the nitrogen atom-containing organic cation has the following formula (3):

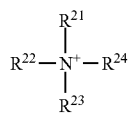
(3)

wherein $R^{21}$ to $R^{24}$ are each independently an alkyl group having 1 to 20 carbon atoms or an alkoxyalkyl group of —$(CH_2)_k$—OR, k is 1 or 2, R is a methyl group or an ethyl group, any two of $R^{21}$ to $R^{24}$ may be bonded to each other to form a ring with a nitrogen atom to which they are bonded, and any two of $R^{21}$ to $R^{24}$ may be bonded to each other to form a ring with a nitrogen atom to which they are bonded, and the remaining two may also be bonded to each other to form a spiro ring having a nitrogen atom as a spiro atom.

2. The salt according to claim 1, wherein $R^1$ to $R^3$ are the same group.

3. The salt according to claim 2, wherein $R^1$ to $R^3$ are a methyl group.

4. A silyl ether-containing sulfonate salt comprising:
an anion having the following formula (1); and
a cation,

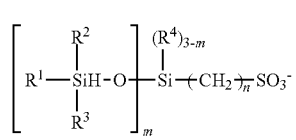
(1)

wherein:
$R^1$ to $R^4$ are each independently an alkyl group having 1 to 4 carbon atoms;
m is an integer of 1 to 3; and
n is an integer of 2 to 8,
wherein $R^1$ is a group different from $R^2$ and $R^3$, and $R^2$ and $R^3$ are the same group.

5. The salt according to claim 4, wherein $R^1$ is an alkyl group having 2 to 4 carbon atoms, and $R^2$ and $R^3$ are a methyl group.

6. The salt according to claim 1, wherein m is 1 or 2.

7. The salt according to claim 1, wherein $R^4$ is a methyl group.

8. The salt of claim 1, wherein n is 2 or 3.

9. The salt according to claim 1, wherein the salt is an ionic liquid having a melting point of 100° C. or lower.

10. The salt according to claim 9, wherein the salt is an ionic liquid having a melting point of 25° C. or lower.

* * * * *